(12) United States Patent
Hatada et al.

(10) Patent No.: US 6,338,959 B1
(45) Date of Patent: Jan. 15, 2002

(54) GENE FOR ENZYME HAVING BOTH ALKALINE PULLULANASE AND ALKALINE α-AMYLASE ACTIVITIES

(75) Inventors: Yuji Hatada; Kazuaki Igarashi; Katsuya Ozaki; Katsutoshi Ara; Shuji Kawai; Susumu Ito, all of Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/514,302

(22) Filed: Feb. 28, 2000

Related U.S. Application Data

(62) Division of application No. 08/952,084, filed as application No. PCT/JP96/01243 on May 10, 1996, now abandoned.

(30) Foreign Application Priority Data

May 10, 1995 (JP) .............................................. 7-111547

(51) Int. Cl.[7] .............................. C12N 9/28; C12N 1/21; C12N 9/26; C12N 15/52; C07H 21/04
(52) U.S. Cl. .................... 435/202; 435/201; 435/252.3; 435/252.31; 435/320.1; 536/23.2
(58) Field of Search ................................ 435/202, 201, 435/252.3, 252.31, 320.1; 536/23.2

(56) References Cited

U.S. PATENT DOCUMENTS 5,147,796 A 9/1992 Ara et al. ................... 435/210

FOREIGN PATENT DOCUMENTS

EP 0418835 A1 3/1991
WO 9419468 A1 9/1994

OTHER PUBLICATIONS

Lee et al., *Applied and Environmental Microbiology*, vol. 60, pp. 3764–3773 (1994).
DMBL Database, EMPRO:MSP207 AAM; Accession No. X55799 (Apr. 1993).
Ara et al., *Biochimica et Biophysica Acta*, vol. 1243, pp. 315–324 (1995).
Kim et al., *Eur. J. Biochem*, vol. 227, pp. 687–693 (1995).
Saha et al., *Enzyme Microb. Technol.*, vol. 11, pp. 760–764 (1989).

*Primary Examiner*—Elizabeth Slobodyansky
(74) *Attorney, Agent, or Firm*—Birch, Stewart, Kolasch & Birch, LLP

(57) ABSTRACT

The present invention provides a DNA fragment encoding alkaline pullulanase exhibiting alkaline α-amylase activity, alkaline α-amylase possessing both an amino acid sequence described in SEQ ID NO:3 and a DNA fragment encoding the amylase, alkaline pullulanase possessing both an amino acid sequence described in SEQ ID NO:4 and a DNA fragment encoding the pullulanase, recombinant DNAs containing these DNA fragments, and transformed microorganisms harboring the recombinant DNAs. The technique of the present invention enables mass production of alkaline pullulanase exhibiting alkaline α-amylase activity.

8 Claims, 6 Drawing Sheets

| | |
|---|---|
| primer 1 | CTGCAGGTAT CGGTAAATAC GGTG |
| primer 2 | TGACGTAACG AATCTTGCTC TAGA |
| primer 3 | TCTAGAGCAT TATCAAAAAT TACT |
| primer 4 | CCGGAACTGA GAATCAAAGA ATTC |
| primer 5 | GAATTCGGAA ATCGCCATGA GGGA |
| primer 6 | GTGGATGGTA ATGAAATTCT AGA |
| primer A | TCTAGATGTG CAATTTTGCG CAAAC |
| primer B | AAGCTTGGGG CAGAATTGCA TGAAG |

FIG.6

SEQUENCE LISTING

```
<160> NUMBER OF SEQ ID NOS: 14

<210> SEQ ID NO 1
<211> LENGTH: 6142
<212> TYPE: DNA
<213> ORGANISM: Bacillus sp.
<220> FEATURE:
<221> NAME/KEY: CDS
<222> LOCATION: (145)..(5958)
<220> FEATURE:
<221> NAME/KEY: sig_peptide
<222> LOCATION: (145)..(240)
<220> FEATURE:
<221> NAME/KEY: mat_peptide
<222> LOCATION: (241)..(5958)

<400> SEQUENCE: 1
tctagatgtg caattttgcg caaacgattt cacatttaca taaacaatct tggcatcaat      60
taaattattt attgtgcaac tttgtgcaaa cgcttccaca ttttagcaag aaatgcaaat     120
cattgtatgg aaagggcag ggat atg aag aaa agg ttt caa agg ggt atg         171
                         Met Lys Lys Arg Phe Gln Arg Gly Met
                             -30                     -25 gct ggt tta ctt tct att tta ctt att gtt tcc atg ttt gca ggc tat       219
Ala Gly Leu Leu Ser Ile Leu Leu Ile Val Ser Met Phe Ala Gly Tyr
```

|  |  |  |  |  |  |  |  |  |  |  |  |  |  |  |  |
|---|---|---|---|---|---|---|---|---|---|---|---|---|---|---|---|
| | -20 | | | | -15 | | | | | -10 | | | | | |
| cta | ccg | gca | aga | gca | gcg | gcc | gaa | acg | gga | gac | aag | cgg | ata | gaa ttc | 267 |
| Leu | Pro | Ala | Arg | Ala | Ala | Ala | Glu | Thr | Gly | Asp | Lys | Arg | Ile | Glu Phe | |
| | | -5 | | | | -1 | 1 | | | | 5 | | | | |
| agt | tat | gaa | cgg | cca | gat | gga | aat | tat | gaa | ggc | tgg | aat | tta | tgg gtc | 315 |
| Ser | Tyr | Glu | Arg | Pro | Asp | Gly | Asn | Tyr | Glu | Gly | Trp | Asn | Leu | Trp Val | |
| | 10 | | | | | 15 | | | | 20 | | | | 25 | |
| tgg | gga | act | ggt | gtg | aag | gat | gac | cag | ata | gac | ttt | aca | gaa | ttc aag | 363 |
| Trp | Gly | Thr | Gly | Val | Lys | Asp | Asp | Gln | Ile | Asp | Phe | Thr | Glu | Phe Lys | |
| | | | 30 | | | | | 35 | | | | | 40 | | |
| gaa | ggc | aag | gca | tat | gcc | gac | ata | gca | gta | agc | gat | aat | gcg | gat aaa | 411 |
| Glu | Gly | Lys | Ala | Tyr | Ala | Asp | Ile | Ala | Val | Ser | Asp | Asn | Ala | Asp Lys | |
| | | | 45 | | | | 50 | | | | | 55 | | | |
| gtc | ggt | ttc | att | atc | cgt | aaa | ggg | gat | tgg | gaa | gaa | aag | gac | ttt gat | 459 |
| Val | Gly | Phe | Ile | Ile | Arg | Lys | Gly | Asp | Trp | Glu | Glu | Lys | Asp | Phe Asp | |
| | | 60 | | | | | 65 | | | | | 70 | | | |
| ggg | gac | agg | tcg | att | acg | atc | aat | aag | atc | gat | aac | atc | acc | aaa gtg | 507 |
| Gly | Asp | Arg | Ser | Ile | Thr | Ile | Asn | Lys | Ile | Asp | Asn | Ile | Thr | Lys Val | |
| | 75 | | | | | 80 | | | | | 85 | | | | |
| cat | gta | aca | agc | cag | cag | gaa | aaa | ttc | ggg | caa | att | cct | gac | ggc agc | 555 |
| His | Val | Thr | Ser | Gln | Gln | Glu | Lys | Phe | Gly | Gln | Ile | Pro | Asp | Gly Ser | |
| 90 | | | | | 95 | | | | | 100 | | | | | 105 |
| cca | cct | gtt | gtt | gcg | gac | ggg | aat | gct | gac | ttc | ttt | ttc | cgt | gat aaa | 603 |
| Pro | Pro | Val | Val | Ala | Asp | Gly | Asn | Ala | Asp | Phe | Phe | Phe | Arg | Asp Lys | |
| | | | | 110 | | | | | 115 | | | | | 120 | |
| gaa | ctg | tac | gca | gca | gga | gaa | atg | gat | aag | gtt | gag | aaa | gtc | gaa ctg | 651 |
| Glu | Leu | Tyr | Ala | Ala | Gly | Glu | Met | Asp | Lys | Val | Glu | Lys | Val | Glu Leu | |
| | | | 125 | | | | | 130 | | | | | 135 | | |
| tcc | att | tta | ggc | gaa | aaa | tac | gag | atg | aat | ggt | gag | ccg | gaa | aag gag | 699 |
| Ser | Ile | Leu | Gly | Glu | Lys | Tyr | Glu | Met | Asn | Gly | Glu | Pro | Glu | Lys Glu | |
| | | 140 | | | | | 145 | | | | | 150 | | | |
| cgt | ttt | aca | tat | aca | tta | agc | gat | ctt | cct | aca | ggc | gag | cat | gaa tat | 747 |
| Arg | Phe | Thr | Tyr | Thr | Leu | Ser | Asp | Leu | Pro | Thr | Gly | Glu | His | Glu Tyr | |
| | 155 | | | | | 160 | | | | | 165 | | | | |
| act | tat | ttg | gtg | aca | gtg | gat | gga | cag | aca | gag | gaa | gtt | acc | gat cca | 795 |
| Thr | Tyr | Leu | Val | Thr | Val | Asp | Gly | Gln | Thr | Glu | Glu | Val | Thr | Asp Pro | |
| 170 | | | | | 175 | | | | | 180 | | | | | 185 |
| tat | aac | acg | gtt | gat | gga | agg | tct | gtt | gtg | gag | tat | gtg | aca | tcc gat | 843 |
| Tyr | Asn | Thr | Val | Asp | Gly | Arg | Ser | Val | Val | Glu | Tyr | Val | Thr | Ser Asp | |
| | | | 190 | | | | | 195 | | | | | 200 | | |
| gtg | caa | gta | tcg | gct | tca | ttt | ata | ccc | gca | aag | gtt | gat | tat | aac cag | 891 |
| Val | Gln | Val | Ser | Ala | Ser | Phe | Ile | Pro | Ala | Lys | Val | Asp | Tyr | Asn Gln | |
| | | 205 | | | | | 210 | | | | | 215 | | | |
| aac | gct | gtg | gtg | aag | gta | gac | atc | gaa | tca | gaa | acg | gag | aca | aaa atc | 939 |
| Asn | Ala | Val | Val | Lys | Val | Asp | Ile | Glu | Ser | Glu | Thr | Glu | Thr | Lys Ile | |
| | 220 | | | | | 225 | | | | | 230 | | | | |
| cgt | gag | atg | tct | atc | aat | ctt | tca | gaa | atc | ggc | ggc | aaa | gag | aaa gca | 987 |
| Arg | Glu | Met | Ser | Ile | Asn | Leu | Ser | Glu | Ile | Gly | Gly | Lys | Glu | Lys Ala | |
| | 235 | | | | | 240 | | | | | 245 | | | | |
| acc | att | gat | cct | gcg | ctg | aat | gaa | ttg | aca | gtt | gcg | gtc | aag | caa ggt | 1035 |
| Thr | Ile | Asp | Pro | Ala | Leu | Asn | Glu | Leu | Thr | Val | Ala | Val | Lys | Gln Gly | |
| 250 | | | | | 255 | | | | | 260 | | | | | 265 |
| gtg | acg | gca | ggt | gtg | aaa | aac | ttg | cct | atc | act | gcg | att | gat | gaa ttc | 1083 |
| Val | Thr | Ala | Gly | Val | Lys | Asn | Leu | Pro | Ile | Thr | Ala | Ile | Asp | Glu Phe | |
| | | | 270 | | | | | 275 | | | | | 280 | | |
| gga | aat | cgc | cat | gag | gga | tct | gct | acc | tta | gaa | gtt | cag | gcg | cgt act | 1131 |
| Gly | Asn | Arg | His | Glu | Gly | Ser | Ala | Thr | Leu | Glu | Val | Gln | Ala | Arg Thr | |
| | | 285 | | | | | 290 | | | | | 295 | | | |
| att | aca | ggt | gaa | aaa | gca | gat | ttc | gac | tgg | gat | cag | tct | gtg | gtt tat | 1179 |

```
Ile Thr Gly Glu Lys Ala Asp Phe Asp Trp Asp Gln Ser Val Val Tyr
        300                 305                 310 ttt atg ctg aca gat cga ttc ttt gat ggg gat tca tcg aac aat gac      1227
Phe Met Leu Thr Asp Arg Phe Phe Asp Gly Asp Ser Ser Asn Asn Asp
        315                 320                 325 cct cat ggt att ggc tat gac aca agc aag tct ggt aca tac caa ggc      1275
Pro His Gly Ile Gly Tyr Asp Thr Ser Lys Ser Gly Thr Tyr Gln Gly
330                 335                 340                 345 gga gat ttt aag ggg atc acg caa agg ctt gat tac ttg gac gag ctt      1323
Gly Asp Phe Lys Gly Ile Thr Gln Arg Leu Asp Tyr Leu Asp Glu Leu
                350                 355                 360 gga atc aat acg atc tgg atc agt ccg gtt gtc gat aat atc aaa ttt      1371
Gly Ile Asn Thr Ile Trp Ile Ser Pro Val Val Asp Asn Ile Lys Phe
            365                 370                 375 gat gtt cga cac agt gaa gga cct gat aca cca tat tat gct tac cac      1419
Asp Val Arg His Ser Glu Gly Pro Asp Thr Pro Tyr Tyr Ala Tyr His
        380                 385                 390 ggc tat tgg gcg gat aat ttc ggg gaa ttg aac ccg cat ttc ggt tcc      1467
Gly Tyr Trp Ala Asp Asn Phe Gly Glu Leu Asn Pro His Phe Gly Ser
    395                 400                 405 atg gcg gat ttc cat gaa atg att gat gcg gca cat gaa cgc ggc att      1515
Met Ala Asp Phe His Glu Met Ile Asp Ala Ala His Glu Arg Gly Ile
410                 415                 420                 425 aaa atc atg gtt gat gtg gtg ttg aat cac act ggt tat gga ttg aaa      1563
Lys Ile Met Val Asp Val Val Leu Asn His Thr Gly Tyr Gly Leu Lys
                430                 435                 440 cca ggt gac agc agc agt gtg gcg aac ttc ccg aca gat gag gac cga      1611
Pro Gly Asp Ser Ser Ser Val Ala Asn Phe Pro Thr Asp Glu Asp Arg
            445                 450                 455 gct cgc ttt gac gga atg ctt cgt gat ggc gga tct ggt gaa gtt cga      1659
Ala Arg Phe Asp Gly Met Leu Arg Asp Gly Gly Ser Gly Glu Val Arg
        460                 465                 470 ggc gag ctt gct ggc ctt cca gat ttt ctg acg gaa aac ccg gat gtc      1707
Gly Glu Leu Ala Gly Leu Pro Asp Phe Leu Thr Glu Asn Pro Asp Val
    475                 480                 485 cgt gaa cag gtg gtg caa tgg cag acg gac tgg atc gaa aag tcc agg      1755
Arg Glu Gln Val Val Gln Trp Gln Thr Asp Trp Ile Glu Lys Ser Arg
490                 495                 500                 505 acg gca aag ggc aac acc atc gat tat ttc cgt gtc gac acc gtc aag      1803
Thr Ala Lys Gly Asn Thr Ile Asp Tyr Phe Arg Val Asp Thr Val Lys
                510                 515                 520 cat gtg gaa gac acc act tgg atg gcg ttt aaa aat gct ttg aca aaa      1851
His Val Glu Asp Thr Thr Trp Met Ala Phe Lys Asn Ala Leu Thr Lys
            525                 530                 535 gcg atg ccg gaa cac aag ctg att ggg gaa gca tgg gga gca aat gtc      1899
Ala Met Pro Glu His Lys Leu Ile Gly Glu Ala Trp Gly Ala Asn Val
        540                 545                 550 aat gac gac cta ggt tat ctg aac agc gga atg atg gat tct tta ctg      1947
Asn Asp Asp Leu Gly Tyr Leu Asn Ser Gly Met Met Asp Ser Leu Leu
    555                 560                 565 gat ttt gat ttc aaa aat tat gcc cgt gac ttt gca aac gga cag ctg      1995
Asp Phe Asp Phe Lys Asn Tyr Ala Arg Asp Phe Ala Asn Gly Gln Leu
570                 575                 580                 585 gat gcg gtt cag caa aaa ctt gag gcg cgt aac agc aag ttg aac aat      2043
Asp Ala Val Gln Gln Lys Leu Glu Ala Arg Asn Ser Lys Leu Asn Asn
                590                 595                 600 act gca aca ctt ggt caa ttt tta gga agc cat gac gaa gac cgc ttc      2091
Thr Ala Thr Leu Gly Gln Phe Leu Gly Ser His Asp Glu Asp Arg Phe
            605                 610                 615
```

```
tat gag gtg gtg gaa gga gac ctt ggc aag tat caa gtt gct gca tcc    2139
Tyr Glu Val Val Glu Gly Asp Leu Gly Lys Tyr Gln Val Ala Ala Ser
        620                 625                 630 ctt caa ctg acg gca aag ggt cag cct gtt atc tat tac gga gaa gag    2187
Leu Gln Leu Thr Ala Lys Gly Gln Pro Val Ile Tyr Tyr Gly Glu Glu
    635                 640                 645 ctg ggc ttg cct ggt aag aac gat tat ccg tat tat acg aac cgc cag    2235
Leu Gly Leu Pro Gly Lys Asn Asp Tyr Pro Tyr Tyr Thr Asn Arg Gln
650                 655                 660                 665 aac atg cct tgg gat gat gtg gat ggt aat gaa att cta gag cat tat    2283
Asn Met Pro Trp Asp Asp Val Asp Gly Asn Glu Ile Leu Glu His Tyr
                670                 675                 680 caa aaa tta ctg gca ttc cgt aat gat aat ccg aac aca ttt gct aaa    2331
Gln Lys Leu Leu Ala Phe Arg Asn Asp Asn Pro Asn Thr Phe Ala Lys
            685                 690                 695 gga gac cgc aaa aag gta gcg gga tct gac agt gaa gga tat ctt tta    2379
Gly Asp Arg Lys Lys Val Ala Gly Ser Asp Ser Glu Gly Tyr Leu Leu
        700                 705                 710 ttt tca cgg acg tac ggg gaa aat tcc gtt tat gta ggt ttg aat acg    2427
Phe Ser Arg Thr Tyr Gly Glu Asn Ser Val Tyr Val Gly Leu Asn Thr
    715                 720                 725 gaa gct gct gcg aaa gac gta acc ttg aac ttc ggt tct tca gaa gca    2475
Glu Ala Ala Ala Lys Asp Val Thr Leu Asn Phe Gly Ser Ser Glu Ala
730                 735                 740                 745 gtg gtg acg gac cgc tat tcc ggt cag gag tac caa gca aat gaa gaa    2523
Val Val Thr Asp Arg Tyr Ser Gly Gln Glu Tyr Gln Ala Asn Glu Glu
                750                 755                 760 ggc caa gtg acg ttc tct att ccg gcg atg gaa gac ggg gga acg gtc    2571
Gly Gln Val Thr Phe Ser Ile Pro Ala Met Glu Asp Gly Gly Thr Val
            765                 770                 775 ctg ctt gaa gtg gaa aat gga gca gtg cca cct gtg gag gaa gaa cca    2619
Leu Leu Glu Val Glu Asn Gly Ala Val Pro Pro Val Glu Glu Glu Pro
        780                 785                 790 act gag cca ggt gaa atc gaa gaa aac acg ctt cgg att cac tac cag    2667
Thr Glu Pro Gly Glu Ile Glu Glu Asn Thr Leu Arg Ile His Tyr Gln
    795                 800                 805 cgc aca gac aac agc tac gaa aac ctt ggt cta tgg tta tgg gga gac    2715
Arg Thr Asp Asn Ser Tyr Glu Asn Leu Gly Leu Trp Leu Trp Gly Asp
810                 815                 820                 825 gtc gcg gca cca tct gaa aac tgg cca tca ggc ggc aca ccg ttc caa    2763
Val Ala Ala Pro Ser Glu Asn Trp Pro Ser Gly Gly Thr Pro Phe Gln
                830                 835                 840 gca ggt aat gta aca gac tat ggt gca tat gtc gat gtg gaa ttg gca    2811
Ala Gly Asn Val Thr Asp Tyr Gly Ala Tyr Val Asp Val Glu Leu Ala
            845                 850                 855 gaa gat gct caa aat att gga ttc ctt gtt ttg aac acc aca aac ggt    2859
Glu Asp Ala Gln Asn Ile Gly Phe Leu Val Leu Asn Thr Thr Asn Gly
        860                 865                 870 gac aag gac ggc ggc gac aaa gca gta gaa ttg ttc agt ccg gat tta    2907
Asp Lys Asp Gly Gly Asp Lys Ala Val Glu Leu Phe Ser Pro Asp Leu
    875                 880                 885 aat gag att tgg atc aaa caa ggc tct gat gaa gta ttt tta tat gaa    2955
Asn Glu Ile Trp Ile Lys Gln Gly Ser Asp Glu Val Phe Leu Tyr Glu
890                 895                 900                 905 ccg gtg gac ctt ccg gca aat acg gtc cgc att cat tat gaa aga acc    3003
Pro Val Asp Leu Pro Ala Asn Thr Val Arg Ile His Tyr Glu Arg Thr
                910                 915                 920 aat gcc gac tat gaa ggc tgg ggg tta tgg aac tgg gag gat gtc gag    3051
Asn Ala Asp Tyr Glu Gly Trp Gly Leu Trp Asn Trp Glu Asp Val Glu
            925                 930                 935
```

```
tcc cca tct gac ggg tgg ccg aac ggt gcc gca gat gct gca ggt atc      3099
Ser Pro Ser Asp Gly Trp Pro Asn Gly Ala Ala Asp Ala Ala Gly Ile
        940                 945                 950 ggt aaa tac ggt gct tac tac gac atc aag ctg aaa gaa gat gct aat      3147
Gly Lys Tyr Gly Ala Tyr Tyr Asp Ile Lys Leu Lys Glu Asp Ala Asn
955                 960                 965 aaa att ggt ttc ctt ttt gtg aac aaa caa tct ggt ggc caa acg gga      3195
Lys Ile Gly Phe Leu Phe Val Asn Lys Gln Ser Gly Gly Gln Thr Gly
970                 975                 980                 985 gat atg acg ttt gat atg ctg aaa caa tac aac caa ctt ttt gta aaa      3243
Asp Met Thr Phe Asp Met Leu Lys Gln Tyr Asn Gln Leu Phe Val Lys
                990                 995                 1000 gag ggc gag gac aag gtc tac acc aat cct tac ggg acc gtg cca ttg      3291
Glu Gly Glu Asp Lys Val Tyr Thr Asn Pro Tyr Gly Thr Val Pro Leu
            1005                1010                1015 gcg ctt gtg tct gga gag gta ttg tca gac aag ttg atc agt ctt act      3339
Ala Leu Val Ser Gly Glu Val Leu Ser Asp Lys Leu Ile Ser Leu Thr
        1020                1025                1030 ttt acc agg aca gaa gga ttg gat ttg gag gaa ttg aaa gaa cag cta      3387
Phe Thr Arg Thr Glu Gly Leu Asp Leu Glu Glu Leu Lys Glu Gln Leu
    1035                1040                1045 gaa atc aag gat gtg gac ggg aac gat gtt tcg ttt aca gat gtg aca      3435
Glu Ile Lys Asp Val Asp Gly Asn Asp Val Ser Phe Thr Asp Val Thr
1050                1055                1060                1065 att gaa ggc gag aaa acg gtc cat gtc cac ggc gag ttt gac ttg gag      3483
Ile Glu Gly Glu Lys Thr Val His Val His Gly Glu Phe Asp Leu Glu
                1070                1075                1080 aaa atc ccg ttc tct gtg acc tat ctg gac cgc acc att tct gta aaa      3531
Lys Ile Pro Phe Ser Val Thr Tyr Leu Asp Arg Thr Ile Ser Val Lys
            1085                1090                1095 tca ggc tgg aaa ctg atc gac gaa atg tat gcc tat gat gga aag ctt      3579
Ser Gly Trp Lys Leu Ile Asp Glu Met Tyr Ala Tyr Asp Gly Lys Leu
        1100                1105                1110 ggg gca gaa ttg cat gaa gac ggg acg gct act ttg aaa gta tgg tcg      3627
Gly Ala Glu Leu His Glu Asp Gly Thr Ala Thr Leu Lys Val Trp Ser
    1115                1120                1125 cca aaa gcg gac aat gtg tct gtt gta ctt tat gac aaa gtt gac cag      3675
Pro Lys Ala Asp Asn Val Ser Val Val Leu Tyr Asp Lys Val Asp Gln
1130                1135                1140                1145 aac gag gtt gta gac acc att gaa atg gta aaa ggg gac cgc ggt gtc      3723
Asn Glu Val Val Asp Thr Ile Glu Met Val Lys Gly Asp Arg Gly Val
                1150                1155                1160 tgg tct gta aag cta act aag gat aat aca ggc ctt gat agt ttg aaa      3771
Trp Ser Val Lys Leu Thr Lys Asp Asn Thr Gly Leu Asp Ser Leu Lys
            1165                1170                1175 ggt tac tat tac cac tat gaa atc acg cat ggt gac gta acg aat ctt      3819
Gly Tyr Tyr Tyr His Tyr Glu Ile Thr His Gly Asp Val Thr Asn Leu
        1180                1185                1190 gct cta gat ccg tat gcc aaa tca atg gcg gcg tgg aat aac gaa gcg      3867
Ala Leu Asp Pro Tyr Ala Lys Ser Met Ala Ala Trp Asn Asn Glu Ala
    1195                1200                1205 ggg gac aag gta gga aaa gcg gcg atc gtg gac atc ggc tcc att ggg      3915
Gly Asp Lys Val Gly Lys Ala Ala Ile Val Asp Ile Gly Ser Ile Gly
1210                1215                1220                1225 cct gag ctt gat tat gcc gac atc cct ggc ttt gaa aag cgc gaa gac      3963
Pro Glu Leu Asp Tyr Ala Asp Ile Pro Gly Phe Glu Lys Arg Glu Asp
                1230                1235                1240 acc atc atc tac gag gtg cat gta cgt gac ttc act tcc gac ccg aat      4011
Thr Ile Ile Tyr Glu Val His Val Arg Asp Phe Thr Ser Asp Pro Asn
```

```
                    1245              1250                1255
atc ggt gag gac ctg aag gca cag ttc ggt aca ttt gct tct ttc gtg      4059
Ile Gly Glu Asp Leu Lys Ala Gln Phe Gly Thr Phe Ala Ser Phe Val
        1260              1265                1270 gaa aag ctg gat tac att caa gag tta ggt gtc act cac att caa ttg      4107
Glu Lys Leu Asp Tyr Ile Gln Glu Leu Gly Val Thr His Ile Gln Leu
    1275              1280                1285 ttg cct gtg atg agc tat tat ttc agc aat gaa ttt gag tct ggg gag      4155
Leu Pro Val Met Ser Tyr Tyr Phe Ser Asn Glu Phe Glu Ser Gly Glu
1290              1295                1300              1305 cgc atg ctg gag tat gct tca acg ggg acg aat tac aat tgg ggc tat      4203
Arg Met Leu Glu Tyr Ala Ser Thr Gly Thr Asn Tyr Asn Trp Gly Tyr
            1310              1315                1320 gac ccg cac aat tac ttc tcc tta tcc ggc atg tac tcc gaa aac cct      4251
Asp Pro His Asn Tyr Phe Ser Leu Ser Gly Met Tyr Ser Glu Asn Pro
        1325              1330                1335 gag gac ccg gaa ctg aga atc aaa gaa ttc aag aat ctg atc aac gag      4299
Glu Asp Pro Glu Leu Arg Ile Lys Glu Phe Lys Asn Leu Ile Asn Glu
    1340              1345                1350 att cat aag cgc gac atg ggt gtg gta ctt gat gtg gtg ttt aac cac      4347
Ile His Lys Arg Asp Met Gly Val Val Leu Asp Val Val Phe Asn His
1355              1360                1365 acc gca cag gtt cac att ttc gag gac ctt gta cca aac tac tat cac      4395
Thr Ala Gln Val His Ile Phe Glu Asp Leu Val Pro Asn Tyr Tyr His
1370              1375                1380              1385 ttc atg gat gcg gac gga acc cca aga act agc ttt ggc ggt gga cgt      4443
Phe Met Asp Ala Asp Gly Thr Pro Arg Thr Ser Phe Gly Gly Gly Arg
        1390              1395                1400 ctt gga acg aca cat gaa atg tcc cgc cgt gtg ctc gta gat tcc atc      4491
Leu Gly Thr Thr His Glu Met Ser Arg Arg Val Leu Val Asp Ser Ile
    1405              1410                1415 aag cat tgg gtg gat gaa tat aag gtg gac gga ttc cgt ttt gac atg      4539
Lys His Trp Val Asp Glu Tyr Lys Val Asp Gly Phe Arg Phe Asp Met
        1420              1425                1430 atg ggt gac cat gat gca gag agt att cag att gct ttt gac gaa gcc      4587
Met Gly Asp His Asp Ala Glu Ser Ile Gln Ile Ala Phe Asp Glu Ala
    1435              1440                1445 aaa aaa ttg aac ccg aat atc gtc atg atc ggg gaa ggc tgg gta aca      4635
Lys Lys Leu Asn Pro Asn Ile Val Met Ile Gly Glu Gly Trp Val Thr
1450              1455                1460              1465 ttt gct ggt gac gag ggc gag ccg gtc cag gcg gcc gat caa caa tgg      4683
Phe Ala Gly Asp Glu Gly Glu Pro Val Gln Ala Ala Asp Gln Gln Trp
        1470              1475                1480 atg caa tat acc gaa gca gtg ggt agc ttc tcg gat gaa ttc cgc aac      4731
Met Gln Tyr Thr Glu Ala Val Gly Ser Phe Ser Asp Glu Phe Arg Asn
    1485              1490                1495 gag ctg aaa tcc ggt ttc gga agc gaa gga cag cca cgt ttc atc aca      4779
Glu Leu Lys Ser Gly Phe Gly Ser Glu Gly Gln Pro Arg Phe Ile Thr
        1500              1505                1510 ggt ggc gcg gtc aat gtg caa caa att ttc gat aac atc aaa gca cag      4827
Gly Gly Ala Val Asn Val Gln Gln Ile Phe Asp Asn Ile Lys Ala Gln
    1515              1520                1525 cct cat aac ttt atg gcc gat caa cca ggc gat gtg gtc caa tac atc      4875
Pro His Asn Phe Met Ala Asp Gln Pro Gly Asp Val Val Gln Tyr Ile
1530              1535                1540              1545 gag gcc cat gac aac ctg acg tta tac gat gtc atc gca caa tct atc      4923
Glu Ala His Asp Asn Leu Thr Leu Tyr Asp Val Ile Ala Gln Ser Ile
        1550              1555                1560 aaa aaa gat ccg gaa atc gcg gaa aac gat tta gag att cat aag cgt      4971
```

```
                Lys Lys Asp Pro Glu Ile Ala Glu Asn Asp Leu Glu Ile His Lys Arg
                         1565                1570                1575 att cgc gtg ggt aat gcc atg gtc ttg acg tct caa ggt acg gca ttc      5019
Ile Arg Val Gly Asn Ala Met Val Leu Thr Ser Gln Gly Thr Ala Phe
        1580                1585                1590 tta cac gca gga cag gaa ttt ggt cgt aca aag caa tgg aga gca cct      5067
Leu His Ala Gly Gln Glu Phe Gly Arg Thr Lys Gln Trp Arg Ala Pro
    1595                1600                1605 gca acg gag gca ccg tac aag tct acg tat atg aca gat gct gat ggc      5115
Ala Thr Glu Ala Pro Tyr Lys Ser Thr Tyr Met Thr Asp Ala Asp Gly
1610                1615                1620                1625 aat ccg ttc gtg tat cca tat ttc atc cac gat tcc tat gat tcc tcg      5163
Asn Pro Phe Val Tyr Pro Tyr Phe Ile His Asp Ser Tyr Asp Ser Ser
            1630                1635                1640 gat atc atc aat cgt ttt gat tgg gaa aaa gcg aca gat gcc gag aaa      5211
Asp Ile Ile Asn Arg Phe Asp Trp Glu Lys Ala Thr Asp Ala Glu Lys
        1645                1650                1655 tac cct gtc aac aat gtg aca cgt gac tac acg gca ggc ttg atc gag      5259
Tyr Pro Val Asn Asn Val Thr Arg Asp Tyr Thr Ala Gly Leu Ile Glu
    1660                1665                1670 ctg cgt cgt tca tct gat gct ttc cgt tta ggt tct cgt gaa ttg gtc      5307
Leu Arg Arg Ser Ser Asp Ala Phe Arg Leu Gly Ser Arg Glu Leu Val
1675                1680                1685 gat tcc aat gtg aca atg gtt gat gcc ccg gaa atc aag gag cag gat      5355
Asp Ser Asn Val Thr Met Val Asp Ala Pro Glu Ile Lys Glu Gln Asp
1690                1695                1700                1705 ctc gtt gtt gcc tac cgc agt gtt tcg acg gcc ggt gtg gag tat tac      5403
Leu Val Val Ala Tyr Arg Ser Val Ser Thr Ala Gly Val Glu Tyr Tyr
            1710                1715                1720 aca ttc gtg aat gcg gac act tcc agt aga aca ttg acc tta ggg cag      5451
Thr Phe Val Asn Ala Asp Thr Ser Ser Arg Thr Leu Thr Leu Gly Gln
        1725                1730                1735 gat ttg aca gag ggc gta gtg gtg gtc gat gca gaa gag gct aat gta      5499
Asp Leu Thr Glu Gly Val Val Val Val Asp Ala Glu Glu Ala Asn Val
    1740                1745                1750 gcc ggt gta gct gag cct gct ggt ttc gaa ttg acg gca gaa ggc atc      5547
Ala Gly Val Ala Glu Pro Ala Gly Phe Glu Leu Thr Ala Glu Gly Ile
1755                1760                1765 aca ctt gag cca ttg act acg gtt gtc gtc cgt gta ggc gag cag gaa      5595
Thr Leu Glu Pro Leu Thr Thr Val Val Val Arg Val Gly Glu Gln Glu
1770                1775                1780                1785 ggg aca gac ccg ggt gat ggg gac ggc gat ggc aat acg ccg cca cca      5643
Gly Thr Asp Pro Gly Asp Gly Asp Gly Asp Gly Asn Thr Pro Pro Pro
            1790                1795                1800 ggc gac ggc gat ggc gat gga aac acg cca cca cca ggg gat ggg gat      5691
Gly Asp Gly Asp Gly Asp Gly Asn Thr Pro Pro Pro Gly Asp Gly Asp
        1805                1810                1815 ggc gat gga aac acg cct cct cca ggc aac ggt aat ggc aat aat cca      5739
Gly Asp Gly Asn Thr Pro Pro Pro Gly Asn Gly Asn Gly Asn Asn Pro
    1820                1825                1830 gga aca cca cca gga aag ggt gga gaa aac cct ggt aaa ggc aaa aac      5787
Gly Thr Pro Pro Gly Lys Gly Gly Glu Asn Pro Gly Lys Gly Lys Asn
1835                1840                1845 gac aaa aca ccg cct ggc aaa ggt ggg gac aat cca ggt aag ggg aac      5835
Asp Lys Thr Pro Pro Gly Lys Gly Gly Asp Asn Pro Gly Lys Gly Asn
1850                1855                1860                1865 aag cta cca ctt acc gca acc gga aca ctt aat tac atc ctg ttt ggt      5883
Lys Leu Pro Leu Thr Ala Thr Gly Thr Leu Asn Tyr Ile Leu Phe Gly
            1870                1875                1880
```

```
gca ata atg ttg gtt ctt ggg acg ctg ctg tat cta ggg gtc aga aga    5931
Ala Ile Met Leu Val Leu Gly Thr Leu Leu Tyr Leu Gly Val Arg Arg
        1885                1890                1895 aaa gca gga ttg aaa gaa aaa acc tta taaaaacaac ggaaaagtgt          5978
Lys Ala Gly Leu Lys Glu Lys Thr Leu
        1900                1905 ggcaggggaa tacccgcca cacttttcg ttattataag gcattatttg cttgtagatt    6038
aaggattcgc tataggttat tttgtgtaac gtacattact tttccgttgg gccatattta  6098
ttttccatac cgctcatttt tcttttccat tgggaccaca ttta                   6142
```

<210> SEQ ID NO 2
<211> LENGTH: 1938
<212> TYPE: PRT
<213> ORGANISM: Bacillus sp.

<400> SEQUENCE: 2

```
Met Lys Lys Arg Phe Gln Arg Gly Met Ala Gly Leu Leu Ser Ile Leu
        -30                 -25                 -20

Leu Ile Val Ser Met Phe Ala Gly Tyr Leu Pro Ala Arg Ala Ala Ala
    -15                 -10                  -5                  -1

Glu Thr Gly Asp Lys Arg Ile Glu Phe Ser Tyr Glu Arg Pro Asp Gly
  1                   5                  10                  15

Asn Tyr Glu Gly Trp Asn Leu Trp Val Trp Gly Thr Gly Val Lys Asp
                 20                  25                  30

Asp Gln Ile Asp Phe Thr Glu Phe Lys Glu Gly Lys Ala Tyr Ala Asp
             35                  40                  45

Ile Ala Val Ser Asp Asn Ala Asp Lys Val Gly Phe Ile Ile Arg Lys
         50                  55                  60

Gly Asp Trp Glu Glu Lys Asp Phe Asp Gly Asp Arg Ser Ile Thr Ile
 65                  70                  75                  80

Asn Lys Ile Asp Asn Ile Thr Lys Val His Val Thr Ser Gln Gln Glu
                 85                  90                  95

Lys Phe Gly Gln Ile Pro Asp Gly Ser Pro Val Val Ala Asp Gly
                100                 105                 110

Asn Ala Asp Phe Phe Arg Asp Lys Glu Leu Tyr Ala Ala Gly Glu
            115                 120                 125

Met Asp Lys Val Glu Lys Val Glu Leu Ser Ile Leu Gly Glu Lys Tyr
        130                 135                 140

Glu Met Asn Gly Glu Pro Glu Lys Glu Arg Phe Thr Tyr Thr Leu Ser
145                 150                 155                 160

Asp Leu Pro Thr Gly Glu His Glu Tyr Thr Tyr Leu Val Thr Val Asp
                165                 170                 175

Gly Gln Thr Glu Glu Val Thr Asp Pro Tyr Asn Thr Val Asp Gly Arg
            180                 185                 190

Ser Val Val Glu Tyr Val Thr Ser Asp Val Gln Val Ser Ala Ser Phe
        195                 200                 205

Ile Pro Ala Lys Val Asp Tyr Asn Gln Asn Ala Val Lys Val Asp
    210                 215                 220

Ile Glu Ser Glu Thr Glu Thr Lys Ile Arg Glu Met Ser Ile Asn Leu
225                 230                 235                 240

Ser Glu Ile Gly Gly Lys Glu Lys Ala Thr Ile Asp Pro Ala Leu Asn
                245                 250                 255

Glu Leu Thr Val Ala Val Lys Gln Gly Val Thr Ala Gly Val Lys Asn
            260                 265                 270
```

-continued

```
Leu Pro Ile Thr Ala Ile Asp Glu Phe Gly Asn Arg His Glu Gly Ser
        275                 280                 285

Ala Thr Leu Glu Val Gln Ala Arg Thr Ile Thr Gly Glu Lys Ala Asp
        290                 295                 300

Phe Asp Trp Asp Gln Ser Val Val Tyr Phe Met Leu Thr Asp Arg Phe
305                 310                 315                 320

Phe Asp Gly Asp Ser Ser Asn Asn Asp Pro His Gly Ile Gly Tyr Asp
                325                 330                 335

Thr Ser Lys Ser Gly Thr Tyr Gln Gly Gly Asp Phe Lys Gly Ile Thr
            340                 345                 350

Gln Arg Leu Asp Tyr Leu Asp Glu Leu Gly Ile Asn Thr Ile Trp Ile
        355                 360                 365

Ser Pro Val Val Asp Asn Ile Lys Phe Asp Val Arg His Ser Glu Gly
    370                 375                 380

Pro Asp Thr Pro Tyr Tyr Ala Tyr His Gly Tyr Trp Ala Asp Asn Phe
385                 390                 395                 400

Gly Glu Leu Asn Pro His Phe Gly Ser Met Ala Asp Phe His Glu Met
                405                 410                 415

Ile Asp Ala Ala His Glu Arg Gly Ile Lys Ile Met Val Asp Val Val
                420                 425                 430

Leu Asn His Thr Gly Tyr Gly Leu Lys Pro Gly Asp Ser Ser Ser Val
        435                 440                 445

Ala Asn Phe Pro Thr Asp Glu Asp Arg Ala Arg Phe Asp Gly Met Leu
450                 455                 460

Arg Asp Gly Gly Ser Gly Glu Val Arg Gly Glu Leu Ala Gly Leu Pro
465                 470                 475                 480

Asp Phe Leu Thr Glu Asn Pro Asp Val Arg Glu Gln Val Val Gln Trp
                485                 490                 495

Gln Thr Asp Trp Ile Glu Lys Ser Arg Thr Ala Lys Gly Asn Thr Ile
                500                 505                 510

Asp Tyr Phe Arg Val Asp Thr Val Lys His Val Glu Asp Thr Thr Trp
        515                 520                 525

Met Ala Phe Lys Asn Ala Leu Thr Lys Ala Met Pro Glu His Lys Leu
    530                 535                 540

Ile Gly Glu Ala Trp Gly Ala Asn Val Asn Asp Asp Leu Gly Tyr Leu
545                 550                 555                 560

Asn Ser Gly Met Met Asp Ser Leu Leu Asp Phe Asp Phe Lys Asn Tyr
                565                 570                 575

Ala Arg Asp Phe Ala Asn Gly Gln Leu Asp Ala Val Gln Gln Lys Leu
            580                 585                 590

Glu Ala Arg Asn Ser Lys Leu Asn Asn Thr Ala Thr Leu Gly Gln Phe
        595                 600                 605

Leu Gly Ser His Asp Glu Asp Arg Phe Tyr Glu Val Val Glu Gly Asp
    610                 615                 620

Leu Gly Lys Tyr Gln Val Ala Ala Ser Leu Gln Leu Thr Ala Lys Gly
625                 630                 635                 640

Gln Pro Val Ile Tyr Tyr Gly Glu Glu Leu Gly Leu Pro Gly Lys Asn
                645                 650                 655

Asp Tyr Pro Tyr Tyr Thr Asn Arg Gln Asn Met Pro Trp Asp Asp Val
            660                 665                 670

Asp Gly Asn Glu Ile Leu Glu His Tyr Gln Lys Leu Leu Ala Phe Arg
        675                 680                 685

Asn Asp Asn Pro Asn Thr Phe Ala Lys Gly Asp Arg Lys Lys Val Ala
```

-continued

```
            690                 695                 700
Gly Ser Asp Ser Glu Gly Tyr Leu Leu Phe Ser Arg Thr Tyr Gly Glu
705                 710                 715                 720
Asn Ser Val Tyr Val Gly Leu Asn Thr Glu Ala Ala Lys Asp Val
                725                 730                 735
Thr Leu Asn Phe Gly Ser Ser Glu Ala Val Val Thr Asp Arg Tyr Ser
                740                 745                 750
Gly Gln Glu Tyr Gln Ala Asn Glu Glu Gly Gln Val Thr Phe Ser Ile
                755                 760                 765
Pro Ala Met Glu Asp Gly Gly Thr Val Leu Leu Glu Val Glu Asn Gly
770                 775                 780
Ala Val Pro Pro Val Glu Glu Pro Thr Glu Pro Gly Glu Ile Glu
785                 790                 795                 800
Glu Asn Thr Leu Arg Ile His Tyr Gln Arg Thr Asp Asn Ser Tyr Glu
                805                 810                 815
Asn Leu Gly Leu Trp Leu Trp Gly Asp Val Ala Ala Pro Ser Glu Asn
                820                 825                 830
Trp Pro Ser Gly Gly Thr Pro Phe Gln Ala Gly Asn Val Thr Asp Tyr
                835                 840                 845
Gly Ala Tyr Val Asp Val Glu Leu Ala Glu Asp Ala Gln Asn Ile Gly
                850                 855                 860
Phe Leu Val Leu Asn Thr Thr Asn Gly Asp Lys Asp Gly Gly Asp Lys
865                 870                 875                 880
Ala Val Glu Leu Phe Ser Pro Asp Leu Asn Glu Ile Trp Ile Lys Gln
                885                 890                 895
Gly Ser Asp Glu Val Phe Leu Tyr Glu Pro Val Asp Leu Pro Ala Asn
                900                 905                 910
Thr Val Arg Ile His Tyr Glu Arg Thr Asn Ala Asp Tyr Glu Gly Trp
                915                 920                 925
Gly Leu Trp Asn Trp Glu Asp Val Glu Ser Pro Ser Asp Gly Trp Pro
                930                 935                 940
Asn Gly Ala Ala Asp Ala Ala Gly Ile Gly Lys Tyr Gly Ala Tyr Tyr
945                 950                 955                 960
Asp Ile Lys Leu Lys Glu Asp Ala Asn Lys Ile Gly Phe Leu Phe Val
                965                 970                 975
Asn Lys Gln Ser Gly Gly Gln Thr Gly Asp Met Thr Phe Asp Met Leu
                980                 985                 990
Lys Gln Tyr Asn Gln Leu Phe Val Lys Glu Gly Glu Asp Lys Val Tyr
                995                 1000                1005
Thr Asn Pro Tyr Gly Thr Val Pro Leu Ala Leu Val Ser Gly Glu Val
    1010                1015                1020
Leu Ser Asp Lys Leu Ile Ser Leu Thr Phe Thr Arg Thr Glu Gly Leu
025                 1030                1035                1040
Asp Leu Glu Glu Leu Lys Glu Gln Leu Glu Ile Lys Asp Val Asp Gly
                1045                1050                1055
Asn Asp Val Ser Phe Thr Asp Val Thr Ile Glu Gly Glu Lys Thr Val
            1060                1065                1070
His Val His Gly Glu Phe Asp Leu Glu Lys Ile Pro Phe Ser Val Thr
        1075                1080                1085
Tyr Leu Asp Arg Thr Ile Ser Val Lys Ser Gly Trp Lys Leu Ile Asp
    1090                1095                1100
Glu Met Tyr Ala Tyr Asp Gly Lys Leu Gly Ala Glu Leu His Glu Asp
105                 1110                1115                1120
```

-continued

```
Gly Thr Ala Thr Leu Lys Val Trp Ser Pro Lys Ala Asp Asn Val Ser
                1125                1130                1135
Val Val Leu Tyr Asp Lys Val Asp Gln Asn Glu Val Val Asp Thr Ile
                1140                1145                1150
Glu Met Val Lys Gly Asp Arg Gly Val Trp Ser Val Lys Leu Thr Lys
                1155                1160                1165
Asp Asn Thr Gly Leu Asp Ser Leu Lys Gly Tyr Tyr Tyr His Tyr Glu
 1170                1175                1180
Ile Thr His Gly Asp Val Thr Asn Leu Ala Leu Asp Pro Tyr Ala Lys
 185                1190                1195                1200
Ser Met Ala Ala Trp Asn Asn Glu Ala Gly Asp Lys Val Gly Lys Ala
                1205                1210                1215
Ala Ile Val Asp Ile Gly Ser Ile Gly Pro Glu Leu Asp Tyr Ala Asp
                1220                1225                1230
Ile Pro Gly Phe Glu Lys Arg Asp Thr Ile Ile Tyr Glu Val His
                1235                1240                1245
Val Arg Asp Phe Thr Ser Asp Pro Asn Ile Gly Glu Asp Leu Lys Ala
                1250                1255                1260
Gln Phe Gly Thr Phe Ala Ser Phe Val Glu Lys Leu Asp Tyr Ile Gln
 265                1270                1275                1280
Glu Leu Gly Val Thr His Ile Gln Leu Leu Pro Val Met Ser Tyr Tyr
                1285                1290                1295
Phe Ser Asn Glu Phe Glu Ser Gly Glu Arg Met Leu Glu Tyr Ala Ser
                1300                1305                1310
Thr Gly Thr Asn Tyr Asn Trp Gly Tyr Asp Pro His Asn Tyr Phe Ser
                1315                1320                1325
Leu Ser Gly Met Tyr Ser Glu Asn Pro Glu Asp Pro Glu Leu Arg Ile
                1330                1335                1340
Lys Glu Phe Lys Asn Leu Ile Asn Glu Ile His Lys Arg Asp Met Gly
 345                1350                1355                1360
Val Val Leu Asp Val Val Phe Asn His Thr Ala Gln Val His Ile Phe
                1365                1370                1375
Glu Asp Leu Val Pro Asn Tyr Tyr His Phe Met Asp Ala Asp Gly Thr
                1380                1385                1390
Pro Arg Thr Ser Phe Gly Gly Gly Arg Leu Gly Thr Thr His Glu Met
                1395                1400                1405
Ser Arg Arg Val Leu Val Asp Ser Ile Lys His Trp Val Asp Glu Tyr
                1410                1415                1420
Lys Val Asp Gly Phe Arg Phe Asp Met Met Gly Asp His Asp Ala Glu
 425                1430                1435                1440
Ser Ile Gln Ile Ala Phe Asp Glu Ala Lys Lys Leu Asn Pro Asn Ile
                1445                1450                1455
Val Met Ile Gly Glu Gly Trp Val Thr Phe Ala Gly Asp Glu Gly Glu
                1460                1465                1470
Pro Val Gln Ala Ala Asp Gln Gln Trp Met Gln Tyr Thr Glu Ala Val
                1475                1480                1485
Gly Ser Phe Ser Asp Glu Phe Arg Asn Glu Leu Lys Ser Gly Phe Gly
                1490                1495                1500
Ser Glu Gly Gln Pro Arg Phe Ile Thr Gly Gly Ala Val Asn Val Gln
 505                1510                1515                1520
Gln Ile Phe Asp Asn Ile Lys Ala Gln Pro His Asn Phe Met Ala Asp
                1525                1530                1535
```

-continued

```
Gln Pro Gly Asp Val Gln Tyr Ile Glu Ala His Asp Asn Leu Thr
            1540                1545                1550

Leu Tyr Asp Val Ile Ala Gln Ser Ile Lys Lys Asp Pro Glu Ile Ala
        1555                1560                1565

Glu Asn Asp Leu Glu Ile His Lys Arg Ile Arg Val Gly Asn Ala Met
1570                1575                1580

Val Leu Thr Ser Gln Gly Thr Ala Phe Leu His Ala Gly Gln Glu Phe
585                 1590                1595                1600

Gly Arg Thr Lys Gln Trp Arg Ala Pro Ala Thr Glu Ala Pro Tyr Lys
                1605                1610                1615

Ser Thr Tyr Met Thr Asp Ala Asp Gly Asn Pro Phe Val Tyr Pro Tyr
            1620                1625                1630

Phe Ile His Asp Ser Tyr Asp Ser Asp Ile Ile Asn Arg Phe Asp
        1635                1640                1645

Trp Glu Lys Ala Thr Asp Ala Glu Lys Tyr Pro Val Asn Asn Val Thr
    1650                1655                1660

Arg Asp Tyr Thr Ala Gly Leu Ile Glu Leu Arg Arg Ser Ser Asp Ala
665                 1670                1675                1680

Phe Arg Leu Gly Ser Arg Glu Leu Val Asp Ser Asn Val Thr Met Val
                1685                1690                1695

Asp Ala Pro Glu Ile Lys Glu Gln Asp Leu Val Val Ala Tyr Arg Ser
            1700                1705                1710

Val Ser Thr Ala Gly Val Glu Tyr Tyr Thr Phe Val Asn Ala Asp Thr
        1715                1720                1725

Ser Ser Arg Thr Leu Thr Leu Gly Gln Asp Leu Thr Glu Gly Val Val
    1730                1735                1740

Val Val Asp Ala Glu Glu Ala Asn Val Ala Gly Val Ala Glu Pro Ala
745                 1750                1755                1760

Gly Phe Glu Leu Thr Ala Glu Gly Ile Thr Leu Glu Pro Leu Thr Thr
                1765                1770                1775

Val Val Val Arg Val Gly Glu Gln Glu Gly Thr Asp Pro Gly Asp Gly
            1780                1785                1790

Asp Gly Asp Gly Asn Thr Pro Pro Gly Asp Gly Asp Gly Asp Gly
        1795                1800                1805

Asn Thr Pro Pro Gly Asp Gly Asp Gly Asp Gly Asn Thr Pro Pro
    1810                1815                1820

Pro Gly Asn Gly Asn Gly Asn Asn Pro Gly Thr Pro Pro Gly Lys Gly
825                 1830                1835                1840

Gly Glu Asn Pro Gly Lys Gly Lys Asn Asp Lys Thr Pro Pro Gly Lys
                1845                1850                1855

Gly Gly Asp Asn Pro Gly Lys Gly Asn Lys Leu Pro Leu Thr Ala Thr
            1860                1865                1870

Gly Thr Leu Asn Tyr Ile Leu Phe Gly Ala Ile Met Leu Val Leu Gly
        1875                1880                1885

Thr Leu Leu Tyr Leu Gly Val Arg Arg Lys Ala Gly Leu Lys Glu Lys
    1890                1895                1900

Thr Leu
1905
```

<210> SEQ ID NO 3
<211> LENGTH: 833
<212> TYPE: PRT
<213> ORGANISM: Bacillus sp.

<400> SEQUENCE: 3

```
Met Lys Lys Arg Phe Gln Arg Gly Met Ala Gly Leu Leu Ser Ile Leu
 1               5                  10                  15
Leu Ile Val Ser Met Phe Ala Gly Tyr Leu Pro Ala Arg Ala Ala Ala
             20                  25                  30
Glu Thr Gly Asp Lys Arg Ile Glu Phe Ser Tyr Glu Arg Pro Asp Gly
         35                  40                  45
Asn Tyr Glu Gly Trp Asn Leu Trp Val Trp Gly Thr Gly Val Lys Asp
     50                  55                  60
Asp Gln Ile Asp Phe Thr Glu Phe Lys Glu Gly Lys Ala Tyr Ala Asp
 65                  70                  75                  80
Ile Ala Val Ser Asp Asn Ala Asp Lys Val Gly Phe Ile Ile Arg Lys
             85                  90                  95
Gly Asp Trp Glu Glu Lys Asp Phe Asp Gly Asp Arg Ser Ile Thr Ile
             100                 105                 110
Asn Lys Ile Asp Asn Ile Thr Lys Val His Val Thr Ser Gln Gln Glu
         115                 120                 125
Lys Phe Gly Gln Ile Pro Asp Gly Ser Pro Val Val Ala Asp Gly
     130                 135                 140
Asn Ala Asp Phe Phe Phe Arg Asp Lys Glu Leu Tyr Ala Ala Gly Glu
145                 150                 155                 160
Met Asp Lys Val Glu Lys Val Glu Leu Ser Ile Leu Gly Glu Lys Tyr
             165                 170                 175
Glu Met Asn Gly Glu Pro Glu Lys Glu Arg Phe Thr Tyr Thr Leu Ser
             180                 185                 190
Asp Leu Pro Thr Gly Glu His Glu Tyr Thr Tyr Leu Val Thr Val Asp
         195                 200                 205
Gly Gln Thr Glu Glu Val Thr Asp Pro Tyr Asn Thr Val Asp Gly Arg
     210                 215                 220
Ser Val Val Glu Tyr Val Thr Ser Asp Val Gln Val Ser Ala Ser Phe
225                 230                 235                 240
Ile Pro Ala Lys Val Asp Tyr Asn Gln Asn Ala Val Val Lys Val Asp
             245                 250                 255
Ile Glu Ser Glu Thr Glu Thr Lys Ile Arg Glu Met Ser Ile Asn Leu
             260                 265                 270
Ser Glu Ile Gly Gly Lys Glu Lys Ala Thr Ile Asp Pro Ala Leu Asn
         275                 280                 285
Glu Leu Thr Val Ala Val Lys Gln Gly Val Thr Ala Gly Val Lys Asn
     290                 295                 300
Leu Pro Ile Thr Ala Ile Asp Glu Phe Gly Asn Arg His Glu Gly Ser
305                 310                 315                 320
Ala Thr Leu Glu Val Gln Ala Arg Thr Ile Thr Gly Glu Lys Ala Asp
             325                 330                 335
Phe Asp Trp Asp Gln Ser Val Val Tyr Phe Met Leu Thr Asp Arg Phe
             340                 345                 350
Phe Asp Gly Asp Ser Ser Asn Asn Asp Pro His Gly Ile Gly Tyr Asp
         355                 360                 365
Thr Ser Lys Ser Gly Thr Tyr Gln Gly Gly Asp Phe Lys Gly Ile Thr
     370                 375                 380
Gln Arg Leu Asp Tyr Leu Asp Glu Leu Gly Ile Asn Thr Ile Trp Ile
385                 390                 395                 400
Ser Pro Val Val Asp Asn Ile Lys Phe Asp Val Arg His Ser Glu Gly
             405                 410                 415
```

-continued

```
Pro Asp Thr Pro Tyr Tyr Ala Tyr His Gly Tyr Trp Ala Asp Asn Phe
            420                 425                 430

Gly Glu Leu Asn Pro His Phe Gly Ser Met Ala Asp Phe His Glu Met
            435                 440                 445

Ile Asp Ala Ala His Glu Arg Gly Ile Lys Ile Met Val Asp Val Val
        450                 455                 460

Leu Asn His Thr Gly Tyr Gly Leu Lys Pro Gly Asp Ser Ser Val
465                 470                 475                 480

Ala Asn Phe Pro Thr Asp Glu Asp Arg Ala Arg Phe Asp Gly Met Leu
                485                 490                 495

Arg Asp Gly Gly Ser Gly Glu Val Arg Gly Glu Leu Ala Gly Leu Pro
                500                 505                 510

Asp Phe Leu Thr Glu Asn Pro Asp Val Arg Glu Gln Val Val Gln Trp
            515                 520                 525

Gln Thr Asp Trp Ile Glu Lys Ser Arg Thr Ala Lys Gly Asn Thr Ile
            530                 535                 540

Asp Tyr Phe Arg Val Asp Thr Val Lys His Val Glu Asp Thr Thr Trp
545                 550                 555                 560

Met Ala Phe Lys Asn Ala Leu Thr Lys Ala Met Pro Glu His Lys Leu
                565                 570                 575

Ile Gly Glu Ala Trp Gly Ala Asn Val Asn Asp Asp Leu Gly Tyr Leu
            580                 585                 590

Asn Ser Gly Met Met Asp Ser Leu Leu Asp Phe Asp Phe Lys Asn Tyr
            595                 600                 605

Ala Arg Asp Phe Ala Asn Gly Gln Leu Asp Ala Val Gln Gln Lys Leu
            610                 615                 620

Glu Ala Arg Asn Ser Lys Leu Asn Asn Thr Ala Thr Leu Gly Gln Phe
625                 630                 635                 640

Leu Gly Ser His Asp Glu Asp Arg Phe Tyr Glu Val Val Glu Gly Asp
                645                 650                 655

Leu Gly Lys Tyr Gln Val Ala Ala Ser Leu Gln Leu Thr Ala Lys Gly
                660                 665                 670

Gln Pro Val Ile Tyr Tyr Gly Glu Glu Leu Gly Leu Pro Gly Lys Asn
            675                 680                 685

Asp Tyr Pro Tyr Tyr Thr Asn Arg Gln Asn Met Pro Trp Asp Asp Val
            690                 695                 700

Asp Gly Asn Glu Ile Leu Glu His Tyr Gln Lys Leu Leu Ala Phe Arg
705                 710                 715                 720

Asn Asp Asn Pro Asn Thr Phe Ala Lys Gly Asp Arg Lys Lys Val Ala
                725                 730                 735

Gly Ser Asp Ser Glu Gly Tyr Leu Leu Phe Ser Arg Thr Tyr Gly Glu
                740                 745                 750

Asn Ser Val Tyr Val Gly Leu Asn Thr Glu Ala Ala Lys Asp Val
            755                 760                 765

Thr Leu Asn Phe Gly Ser Ser Glu Ala Val Thr Asp Arg Tyr Ser
            770                 775                 780

Gly Gln Glu Tyr Gln Ala Asn Glu Gly Gln Val Thr Phe Ser Ile
785                 790                 795                 800

Pro Ala Met Glu Asp Gly Gly Thr Val Leu Leu Glu Val Glu Asn Gly
                805                 810                 815

Ala Val Pro Pro Val Glu Glu Pro Thr Glu Pro Gly Glu Ile Glu
            820                 825                 830

Glu
```

-continued

```
<210> SEQ ID NO 4
<211> LENGTH: 893
<212> TYPE: PRT
<213> ORGANISM: Bacillus sp.

<400> SEQUENCE: 4

Thr Val Pro Leu Ala Leu Val Ser Gly Glu Val Leu Ser Asp Lys Leu
 1               5                  10                  15

Ile Ser Leu Thr Phe Thr Arg Thr Glu Gly Leu Asp Leu Glu Glu Leu
             20                  25                  30

Lys Glu Gln Leu Glu Ile Lys Asp Val Asp Gly Asn Asp Val Ser Phe
         35                  40                  45

Thr Asp Val Thr Ile Glu Glu Lys Thr Val His Val His Gly Glu
 50                  55                  60

Phe Asp Leu Glu Lys Ile Pro Phe Ser Val Thr Tyr Leu Asp Arg Thr
 65                  70                  75                  80

Ile Ser Val Lys Ser Gly Trp Lys Leu Ile Asp Glu Met Tyr Ala Tyr
                 85                  90                  95

Asp Gly Lys Leu Gly Ala Glu Leu His Glu Asp Gly Thr Ala Thr Leu
            100                 105                 110

Lys Val Trp Ser Pro Lys Ala Asp Asn Val Ser Val Val Leu Tyr Asp
        115                 120                 125

Lys Val Asp Gln Asn Glu Val Val Asp Thr Ile Glu Met Val Lys Gly
    130                 135                 140

Asp Arg Gly Val Trp Ser Val Lys Leu Thr Lys Asp Asn Thr Gly Leu
145                 150                 155                 160

Asp Ser Leu Lys Gly Tyr Tyr His Tyr Glu Ile Thr His Gly Asp
                165                 170                 175

Val Thr Asn Leu Ala Leu Asp Pro Tyr Ala Lys Ser Met Ala Ala Trp
            180                 185                 190

Asn Asn Glu Ala Gly Asp Lys Val Gly Lys Ala Ala Ile Val Asp Ile
        195                 200                 205

Gly Ser Ile Gly Pro Glu Leu Asp Tyr Ala Asp Ile Pro Gly Phe Glu
    210                 215                 220

Lys Arg Glu Asp Thr Ile Ile Tyr Glu Val His Val Arg Asp Phe Thr
225                 230                 235                 240

Ser Asp Pro Asn Ile Gly Glu Asp Leu Lys Ala Gln Phe Gly Thr Phe
                245                 250                 255

Ala Ser Phe Val Glu Lys Leu Asp Tyr Ile Gln Glu Leu Gly Val Thr
            260                 265                 270

His Ile Gln Leu Leu Pro Val Met Ser Tyr Tyr Phe Ser Asn Glu Phe
        275                 280                 285

Glu Ser Gly Glu Arg Met Leu Glu Tyr Ala Ser Thr Gly Thr Asn Tyr
    290                 295                 300

Asn Trp Gly Tyr Asp Pro His Asn Tyr Phe Ser Leu Ser Gly Met Tyr
305                 310                 315                 320

Ser Glu Asn Pro Glu Asp Pro Glu Leu Arg Ile Lys Glu Phe Lys Asn
                325                 330                 335

Leu Ile Asn Glu Ile His Lys Arg Asp Met Gly Val Val Leu Asp Val
            340                 345                 350

Val Phe Asn His Thr Ala Gln Val His Ile Phe Glu Asp Leu Val Pro
        355                 360                 365

Asn Tyr Tyr His Phe Met Asp Ala Asp Gly Thr Pro Arg Thr Ser Phe
```

-continued

```
            370                 375                 380
Gly Gly Gly Arg Leu Gly Thr Thr His Glu Met Ser Arg Val Leu
385                 390                 395                 400

Val Asp Ser Ile Lys His Trp Val Asp Glu Tyr Lys Val Asp Gly Phe
                405                 410                 415

Arg Phe Asp Met Met Gly Asp His Asp Ala Glu Ser Ile Gln Ile Ala
                420                 425                 430

Phe Asp Glu Ala Lys Lys Leu Asn Pro Asn Ile Val Met Ile Gly Glu
                435                 440                 445

Gly Trp Val Thr Phe Ala Gly Asp Glu Gly Pro Val Gln Ala Ala
                450                 455                 460

Asp Gln Gln Trp Met Gln Tyr Thr Glu Ala Val Gly Ser Phe Ser Asp
465                 470                 475                 480

Glu Phe Arg Asn Glu Leu Lys Ser Gly Phe Gly Ser Glu Gly Gln Pro
                485                 490                 495

Arg Phe Ile Thr Gly Gly Ala Val Asn Val Gln Gln Ile Phe Asp Asn
                500                 505                 510

Ile Lys Ala Gln Pro His Asn Phe Met Ala Asp Gln Pro Gly Asp Val
                515                 520                 525

Val Gln Tyr Ile Glu Ala His Asp Asn Leu Thr Leu Tyr Asp Val Ile
                530                 535                 540

Ala Gln Ser Ile Lys Lys Asp Pro Glu Ile Ala Glu Asn Asp Leu Glu
545                 550                 555                 560

Ile His Lys Arg Ile Arg Val Gly Asn Ala Met Val Leu Thr Ser Gln
                565                 570                 575

Gly Thr Ala Phe Leu His Ala Gly Gln Glu Phe Gly Arg Thr Lys Gln
                580                 585                 590

Trp Arg Ala Pro Ala Thr Glu Ala Pro Tyr Lys Ser Thr Tyr Met Thr
                595                 600                 605

Asp Ala Asp Gly Asn Pro Phe Val Tyr Pro Tyr Phe Ile His Asp Ser
                610                 615                 620

Tyr Asp Ser Ser Asp Ile Ile Asn Arg Phe Asp Trp Glu Lys Ala Thr
625                 630                 635                 640

Asp Ala Glu Lys Tyr Pro Val Asn Asn Val Thr Arg Asp Tyr Thr Ala
                645                 650                 655

Gly Leu Ile Glu Leu Arg Arg Ser Ser Asp Ala Phe Arg Leu Gly Ser
                660                 665                 670

Arg Glu Leu Val Asp Ser Asn Val Thr Met Val Asp Ala Pro Glu Ile
                675                 680                 685

Lys Glu Gln Asp Leu Val Val Ala Tyr Arg Ser Val Ser Thr Ala Gly
                690                 695                 700

Val Glu Tyr Tyr Thr Phe Val Asn Ala Asp Thr Ser Ser Arg Thr Leu
705                 710                 715                 720

Thr Leu Gly Gln Asp Leu Thr Glu Gly Val Val Val Asp Ala Glu
                725                 730                 735

Glu Ala Asn Val Ala Gly Val Ala Glu Pro Ala Gly Phe Glu Leu Thr
                740                 745                 750

Ala Glu Gly Ile Thr Leu Glu Pro Leu Thr Thr Val Val Arg Val
                755                 760                 765

Gly Glu Gln Glu Gly Thr Asp Pro Gly Asp Gly Asp Gly Asn
                770                 775                 780

Thr Pro Pro Pro Gly Asp Gly Asp Gly Asp Gly Asn Thr Pro Pro Pro
785                 790                 795                 800
```

```
Gly Asp Gly Asp Gly Asp Gly Asn Thr Pro Pro Gly Asn Gly Asn
                805                 810                 815

Gly Asn Asn Pro Gly Thr Pro Pro Gly Lys Gly Gly Glu Asn Pro Gly
            820                 825                 830

Lys Gly Lys Asn Asp Lys Thr Pro Pro Gly Lys Gly Gly Asp Asn Pro
        835                 840                 845

Gly Lys Gly Asn Lys Leu Pro Leu Thr Ala Thr Gly Thr Leu Asn Tyr
    850                 855                 860

Ile Leu Phe Gly Ala Ile Met Leu Val Leu Gly Thr Leu Leu Tyr Leu
865                 870                 875                 880

Gly Val Arg Arg Lys Ala Gly Leu Lys Glu Lys Thr Leu
            885                 890

<210> SEQ ID NO 5
<211> LENGTH: 16
<212> TYPE: PRT
<213> ORGANISM: Bacillus sp.

<400> SEQUENCE: 5

Thr Val Pro Leu Ala Leu Val Ser Gly Glu Val Leu Ser Asp Lys Leu
  1               5                  10                  15

<210> SEQ ID NO 6
<211> LENGTH: 14
<212> TYPE: PRT
<213> ORGANISM: Bacillus sp.

<400> SEQUENCE: 6

Glu Thr Gly Asp Lys Arg Ile Glu Phe Ser Tyr Glu Arg Pro
  1               5                  10

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer 1

<400> SEQUENCE: 7
ctgcaggtat cggtaaatac ggtg                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer 2

<400> SEQUENCE: 8
tgacgtaacg aatcttgctc taga                                          24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer 3

<400> SEQUENCE: 9
tctagagcat tatcaaaaat tact                                          24

<210> SEQ ID NO 10
```

```
<211> LENGTH: 24
<212> TYPE: DNA
<213> ORGANISM: Artificial Sequence
<220> FEATURE:
<223> OTHER INFORMATION: Description of Artificial Sequence: Primer 4

<400> SEQUENCE: 10
ccggaactga gaatcaaaga attc                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Primer 5

<400> SEQUENCE: 11
gaattcggaa atcgccatga ggga                                              24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer 6

<400> SEQUENCE: 12
gtggatggta atgaaattct aga                                               23

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Primer A

<400> SEQUENCE: 13
tctagatgtg caattttgcg caaac                                             25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Primer B

<400> SEQUENCE: 14
aagcttgggg cagaattgca tgaag                                             25
```

GENE FOR ENZYME HAVING BOTH ALKALINE PULLULANASE AND ALKALINE α-AMYLASE ACTIVITIES

This application is a divisional of application Ser. No. 08/952,084, filed on Nov. 10, 1997, now abandoned which is a 371 of PCT/JP96/01243, filed May 10, 1996 the entire contents of which are hereby incorporated by reference.

TECHNICAL FIELD

The present invention relates to the gene encoding an enzyme that exhibits both alkaline pullulanase activity and alkaline α-amylase activity (alkaline amylopullulanase), to alkaline α-amylase and alkaline pullulanase obtainable from expression of a fragment of the gene encoding the intact alkaline amylopullulanase, to the gene or fragments thereof encoding these enzymatic activities, and to recombinant DNAs and transformants bearing the gene and fragments thereof.

BACKGROUND ART

Alpha-amylase has long been used in a variety of fields. For example, it has been used for the saccharification of grains and potatoes in the fermentation industry, as starch paste removers in the textile industry, as digestives in the pharmaceutical industry, and for the manufacture of thick malt sugar syrups in the food industry. Alpha-amylase is an enzyme which acts on starch-related polysaccharides such as amylose or amylopectin, cutting solely the α-1,4-glucoside bond of the polysaccharide molecule. Crystalline samples or electrophoretically uniform samples of α-amylase have been obtained from a number of different sources including bacteria, fungi, plant seeds, and animal digestive glands. Pullulanase is an enzyme which hydrolyzes solely the α-1, 6-glucoside bond present in starch, glycogen, amylopectin, and pullulan. Pullulanase was first found in a certain strain of *Aerobacter aerogenes* (Bender, H. and Wallenfels, K., *Biochem. J.*, 334, 79 (1961)), and thereafter, was also found in many other microorganisms including genera Bacillus, Streptococcus and Clostridium. Pullulanase has become of interest in the starch-making industry because of its ability to produce, from starch, maltooligosaccharides such as glucose, maltose, maltotriose, maltopentaose, and maltohexaose when it is used in combination with endo-type amylase and exo-type amylase.

In order to simplify the process of the manufacture of saccharides in which two or more enzymes are used, as described above, pullulanase which also acts on the α-1,4-glucoside bond, in other words, pullulanase exhibiting α-amylase activity, is greatly desired. *Bacillus subtilis* TU strain is known to produce a pullulanase-amylase complex enzyme (Takasaki, Y., *Agric. Biol. Chem.*, 51, 9 (1987), Japanese Patent Publication (kokoku) No. 1-18717). In addition, enzymes exhibiting the above two distinct enzymatic activities or so-called amylopullulanases have been reported for a number of bacteria including *Bacillus circulans* (Japanese Patent Application Laid-open (kokai) No. 64-60376), Bacillus sp. (Saha, B. C., et al., *Enzyme Microb. Technol.*, 11, 760 (1989)), *Thermoanaerobium brockii* (Coleman, R. D. et al., *J. Bacteriol.*, 169, 4302 (1987)), Thermoanaerobium sp. (Plant, A. R., et al., *Appl. Microbiol. Biotechnol.*, 26, 427 (1987)), *Clostridium thermohydrosulfuricum* (Saha, B. C., et al., *Biochem. J.*, 252, 343 (1988)), *Clostridium thermosulfurogenes* (Spreinat, A. et al., *Appl. Microbiol. Biotechnol.*, 33, 511 (1990)), *Thermus aquaticus* (Plant, A. R., et al., *Enzyme Microb. Technol.*, 8, 668 (1986)), Thermus sp. (Nakamura, N et al., *Starch/Starke*, 41, 112 (1989)), *Thermoanaerobacterium saccharolyticum* (Saha, B. C., et al., *Appl. Environ. Microbiol.*, 56, 881 (1990)), and *Pyrococcus furiosus* and *Thermococcus litoralis* (Brown, S. H. and Kelley, R. M., *Appl. Environ. Microbiol.*, 59, 2614 (1993)).

The present inventors have recently discovered that the efficacy of dish-washing detergents and detergents for clothes can be greatly improved, particularly on starch soils, when α-amylase and pullulanase are both incorporated into the detergents (Japanese Patent Application Laid-open (Kokai) No. 2-132193). However, most of the α-amylases and pullulanases previously found in the natural world exhibit maximal and stable enzymatic activities in the neutral to acidic pH ranges, but scarcely work in an alkaline solution of pH 9–10. There exist very few enzymes exhibiting maximal activities in the alkaline pH range (alkaline pullulanases), and only two reports of such enzymes have been published (Nakamura, N. and Horikoshi, K., *Biochim. Bophys. Acta,* 397, 188 (1975), Japanese Patent Publication (kokoku) No. 53 -27786 and Ara et al. Japanese Patent Publication kokoku) No. 6-32613. Furthermore, an enzyme that has both alkaline α-amylase and alkaline pullulanase activities had not been reported until the present inventors discovered that an alkalophilic Bacillus sp. KSM-AP1378 (FERM BP-3048, deposited Jul. 24, 1989 in Fermentation Research Institute, Agency of Industrial Science and Technology of 1–3, Higashi 1-chome, Tsukuba-shi, Ibaraki, 305 Japan) having its optimum pH for growth in the alkaline range produces a novel alkaline amylopullulanase (formerly designated pullulanase Y) that has both alkaline pullulanase and alkaline α-amylase activities. They elucidated that this enzyme is useful as an additive in detergent compositions for automatic dishwashers and in detergent compositions for clothes (Japanese Patent Application Laid-open (kokai) No. 3–290498). Although this enzyme is constituted by a single enzyme molecule, it exhibits both alkaline α-amylase activity and alkaline pullulanase activity. Exploitation of this enzyme has proved very advantageous in culturing the bacteria and in purification of the enzyme, compared to the case in which the two enzymes are independently produced by two different bacteria.

The present inventors have attempted to improve productivity of the alkaline amylopullulanase (formerly designated pullulanase Y) producing bacterium, Bacillus sp. KSM-AP1378, through optimization of culturing methods. Nevertheless, it is still desired to improve further the enzyme productivity of the bacterium so as to advantageously produce the alkaline amylopullulanase on an industrial scale. It is noted that production of the enzyme can be further enhanced using genetic engineering and the activity of the enzyme itself can be improved by altering the gene encoding the enzyme using a protein engineering approach. Applying these approaches requires the gene encoding alkaline amylopullulanase.

Accordingly, an object of the present invention is to provide the gene encoding alkaline amylopullulanase, recombinant DNA comprising the gene, and a transformant harboring the recombinant DNA.

The DNA encoding the alkaline amylopullulanase gene may be further used to produce probes to be used in the isolation of additional, homologous alkaline amylopullulanase genes from other microorganisms. Thus, an additional object of the present invention is to provide a means of screening for and isolating additional alkaline amylopullulanase enzymes.

DISCLOSURE OF THE INVENTION

The present inventors isolated a DNA fragment encoding alkaline amylopullulanase from the chromosomal DNA of an alkalophilic Bacillus strain using shotgun cloning and PCR. When they transformed a microorganism with this DNA fragment ligated to a suitable vector, it was confirmed that the resultant recombinant microorganism produced alkaline amylopullulanase. Moreover, it was found that the amino acid sequence of the alkaline amylopullulanase encoded by the DNA fragment is completely different from those of previously known amylases and pullulanases, and that this enzyme has the feature that the amino terminal moiety of the enzyme molecule is alkaline α-amylase, and the carboxy terminal moiety of the enzyme molecule is alkaline pullulanase. The present invention was accomplished based on this finding.

Accordingly, the present invention provides a DNA fragment encoding alkaline amylopullulanase.

The present invention also provides alkaline α-amylase having the amino acid sequence described in SEQ ID NO:3 provided hereinbelow, as well as a DNA fragment encoding the alkaline α-amylase.

The present invention also provides alkaline pullulanase having the amino acid sequence described in SEQ ID NO:4 provided hereinbelow, as well as a DNA fragment encoding the alkaline pullulanase.

The present invention also provides recombinant DNA comprising a DNA fragment encoding the above-described alkaline amylopullulanase, alkaline α-amylase, or alkaline pullulanase.

The present invention also provides a transformed microorganism harboring recombinant DNA comprising a DNA fragment encoding the above-described alkaline amylopullulanase, alkaline α-amylase, or alkaline pullulanase.

The present invention further provides a method for producing alkaline amylopullulanase, alkaline α-amylase, or alkaline pullulanase, characterized by culturing the above-described transformed microorganism and collecting any one of the expressed enzymes.

BRIEF DESCRIPTION OF THE DRAWINGS

FIG. 6 shows nucleotide sequences of primers used for PCR (SEQ ID NO:7 to 14). Primers 1 (SEQ ID NO:7), 3 (SEQ ID NO:9), 5 (SEQ ID NO:10), and B (SEQ ID NO:14), were used as complementary sequences.

DETAILED DESCRIPTION OF THE PREFERRED EMBODIMENTS

Figure 1:
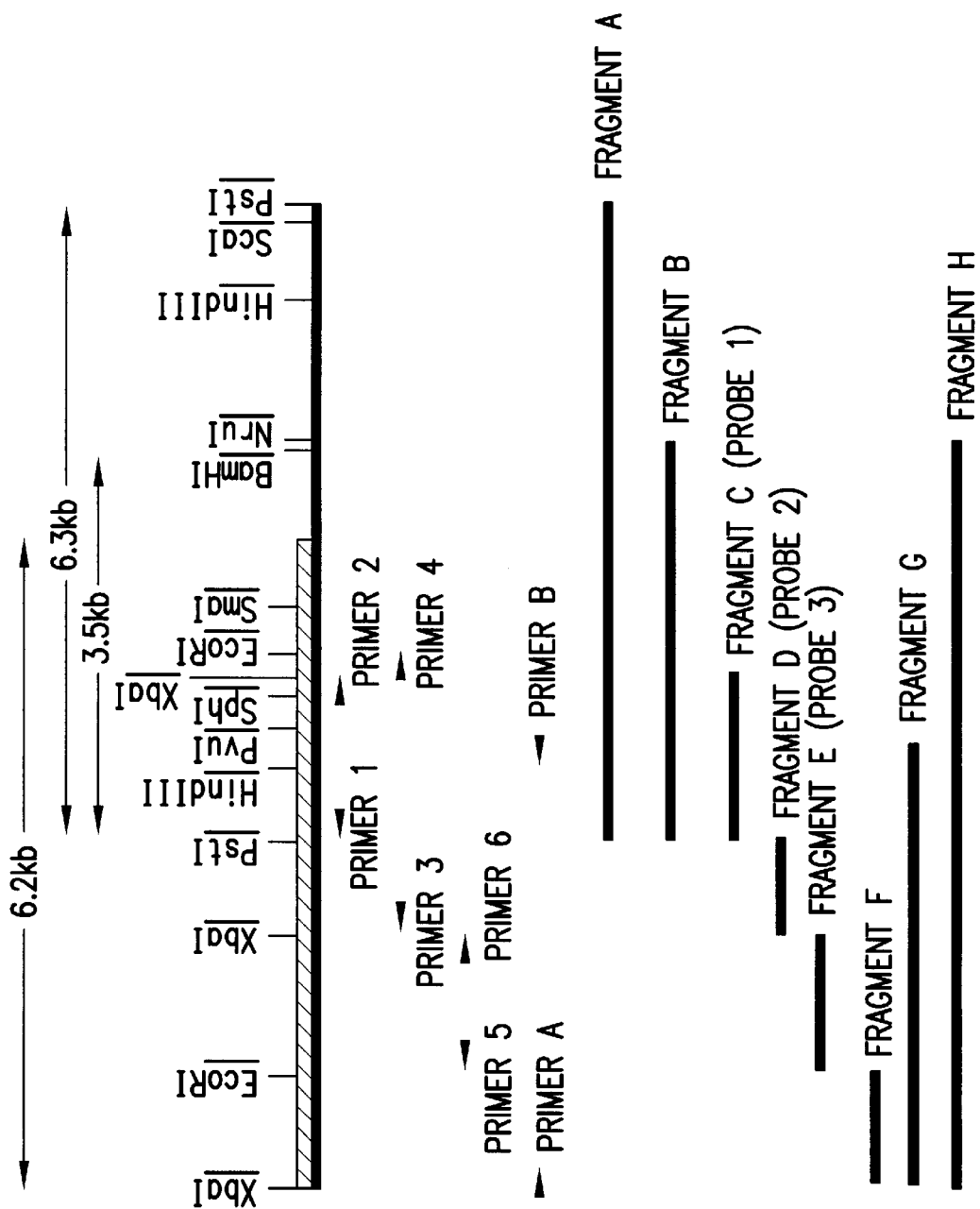
FIG. 1 shows a restriction enzyme map of the alkaline amylopullulanase gene from Bacillus sp. KSM-AP1378 and positions of the primers.

In the present invention, a useful microorganism which serves as an alkaline amylopullulanase gene donor may be, for example, Bacillus sp. KSM-AP1378, which is an alkalophilic Bacillus. This strain was isolated from the soil in the vicinity of the city of Tochigi in Tochigi Prefecture, Japan by the present inventors and identified as a strain producing significant amounts of alkaline amylopullulanase. This strain has,been deposited at the Fermentation Research Institute under BP-3048.

In order to obtain chromosomal DNA from a donor microorganism, methods proposed by Marmur, J. (*J. Mol. Biol.*, 3, 208 (1961)) and by Saito, H. and Miura, K. (*Biochim. Biophys. Acta*, 72, 619 (1963)) may be used. Other similar methods may also be used.

DNA fragments comprising the alkaline amylopullulanase gene are prepared by cleaving the thus-obtained chromosomal DNA using restriction enzymes. Restriction enzymes which may be used are not particularly limited so long as they do not damage the gene. The alkaline amylopullulanase gene may also be obtained by PCR. For example, the gene may be obtained by synthesizing primers having sequences corresponding to those on the upstream side of the 5'-terminus and on the downstream side of the 3'-terminus of the essential region based on the nucleotide sequence described in SEQ ID NO:1, and conducting PCR using, as a template, the chromosomal DNA of an alkaline amylopullulanase-producing microorganism. Alternatively, an intact gene may be obtained by either method of first obtaining an alkaline pullulanase gene fragment from an alkaline amylopullulanase-producing microorganism using any procedure, followed by PCR which amplifies an alkaline α-amylase gene fragment existing on the upstream side of the former fragment, or conversely, via a method of first obtaining an alkaline α-amylase gene, followed by PCR which amplifies an alkaline pullulanase gene fragment existing on the downstream side of the gene.

The thus-prepared genetic fragment is then subjected to cloning. Host/vector systems which may be used are not particularly limited, so far as host bacterial strains express the alkaline amylopullulanase gene of the present invention, that the recombinant DNA can be replicated in the host bacteria, and that the recombinant DNA can stably harbor the integrated gene. For example, members of the EK system in which the host is *E. coli* K-12, and those of the BS system in which the host is *Bacillus subtilis* Marburg may be used. Use of the EK system which encompasses many kinds of vectors and is extensively studied genetically provides good results and thus is preferred. Specific examples of host bacteria include strains HB101, C600, and JM109 of the EK system, and strains BD170, MI11, and ISW1214 of the BS system. Specific examples of vectors include pBR322 and pUC18 of the EK system, and pUB110 and pHY300PLK of the BS system. A recombinant plasmid DNA is created by cleaving a vector with a restriction enzyme followed by ligation with the above-mentioned chromosomal or PCR-amplified DNA fragment. The ligation may be achieved, for example, through the use of a DNA ligase.

Methods for transforming host bacterial strains using recombinant DNA are not particularly limited. For example, a calcium chloride method (Mandel, M. and Higa, A., *J. Mol. Biol.*, 53, 159 (1970)) may be used in the case of hosts of the EK system, and a protoplast method (Chang, C. and Cohen, S. N., *Mol. Gen. Genet.*, 168, 111 (1978)) may be used in the case of hosts of the BS system.

Selection of recombinant microorganisms are performed as follows. First, microorganisms which have been transformed with DNA containing a vector-derived DNA fragment are selected using, as an index, a character such as antibiotics resistance coded on the vector DNA which is not inactivated by insertion of exogenous chromosomal or PCR-amplified DNA fragments. For example, in a specific case in which pBR322 of EK system is used as a vector, and a BamHI fragment of chromosomal DNA is inserted into the BamHI cleavage site of pBR322, the tetracycline resistant gene is inactivated, so a primary selection may be conducted using, as an index, ampicillin resistance without having a BamHI cleavage site in the gene. Subsequently, the selected microorganisms are transferred onto agar plates containing starch or pullulan using, for example, a replica method and are then cultured to form colonies. Colonies are detected that decompose starch, that form halos on the starch-containing agar plate, and that also form halos on the pullulan-containing agar plate.

The recombinant DNA harbored by the thus-obtained recombinant microorganism can be extracted using standard procedures for preparing plasmids or phage DNAs (Maniatis, T. et al., *Molecular Cloning*, Cold Spring Harbor Laboratory, New York (1982)). By cleaving the extracted recombinant DNA using a variety of restriction enzymes and analyzing cleavage patterns by electrophoresis, it is confirmed that the recombinant DNA is a ligated product of the vector DNA and a DNA fragment containing the alkaline amylopullulanase gene.

Fragments encoding the alkaline pullulanase activity, parts of the alkaline amylopullulanase of the present invention, are contained in a DNA fragment of about 9.4 kb, as shown in the restriction enzyme map of FIG. 1, and are present in the segment of about 6.2 kb shown by the cross-hatched bar.

The fragment having a size of about 6.2 kb and containing the alkaline amylopullulanase gene has a nucleotide sequence shown by SEQ ID NO:2. In this sequence, the 5' terminus and 3'terminus correspond to the left-hand side and the right-hand side, respectively, of the fragment of about 6.2 kb. In this sequence is observed an open reading frame (ORF) starting translation at the 145th ATG and coding for a sequence formed of 1938 amino acid residues described in SEQ ID NO:2. Fifteen bases (15b) upstream of the ORF, there exists a sequence GAAAGGGG which is highly complementary to the 3' terminal sequence of the 16S ribosomal RNA of *Bacillus subtilis* (McLaughlin, J. R. et al., *J. Biol. Chem.*, 256, 11283 (1981)). On a further upstream side extending from the 35th nucleotide, there exists a sequence TTTACA . . . 20 b . . . TAAATT which has high homology with the consensus sequence of a $\sigma^A$-type promoter (Gitt, M. A. et al, *J. Biol. Chem.*, 260, 7178 (1985)). On the downstream side of the translation termination codon TAA at the 5959th nucleotide, there exists an inverted repeated sequence (nucleotide Nos. 5961–6015) which is presumably a transcription terminator. In addition, the amino acid sequence of the 14 residues on the amino terminus side in alkaline amylopullulanase obtained through purifying a culture of Bacillus sp. KSM-AP1378 coincides with the sequence extending from the first amino acid (amino acids 1–14 in SEQ ID NO:2) deduced from the nucleotide sequence in the present DNA fragment.

When the nucleotide sequence of the gene of the present invention and a putative amino acid sequence were compared with those of α-amylase and pullulanase known hitherto, it was confirmed that the present gene is a novel one possessing a unique nucleotide sequence, with the amino acid sequence encoded by the gene being different from that of either α-amylase or pullulanase.

Moreover, the gene of the present invention is characterized in that it encodes an enzyme possessing two active centers, one for alkaline α-amylase and the other for alkaline pullulanase, in a single peptide chain of the protein. There is each of four sequences (regions I–IV; Nakajima, R. et al, *Appl. Microbiol. Biotechnol.*, 23, 355 (1986)) observed uniquely for the active center of amylase, amino acids 430–613, and for pullulanase, amino acids 1364–1549. Specifically, in the amino acid sequence of SEQ ID NO:1, region I of alkaline α-amylase=430–435, region II of alkaline α-amylase=514–522, region III of alkaline α-amylase=547–550, region IV of alkaline α-amylase=608–613, region I of alkaline pullulanase=1364–1369, region II of alkaline pullulanase=1428–1436, region III of alkaline pullulanase=1461–1464, region IV of alkaline pullulanase 1544–1549. Moreover, between the structural genes presumably encoding alkaline α-amylase and alkaline pullulanase, respectively, an intervening sequence formed of 33 amino acids appears twice (in the amino acid of Sequence No. 2, 802–834 and 912–944). Therefore, by using the characteristic feature, it is also possible to express the alkaline α-amylase moiety and the alkaline pullulanase moiety in an independent manner. For example, if a gene encoding the amino acids stretching from the initiation codon to directly before the intervening sequence is inserted into a plasmid vector DNA and is introduced into a suitable host bacterium, it is possible to produce alkaline α-amylase alone (Sequence NO. 3). Likewise, if a gene containing the amino acids stretching directly after the intervening sequence to the 1906th amino acid is inserted into a plasmid vector DNA and is introduced into a suitable host bacterium, it is possible to produce alkaline pullulanase alone (SEQ ID NO:4).

Figure 2:
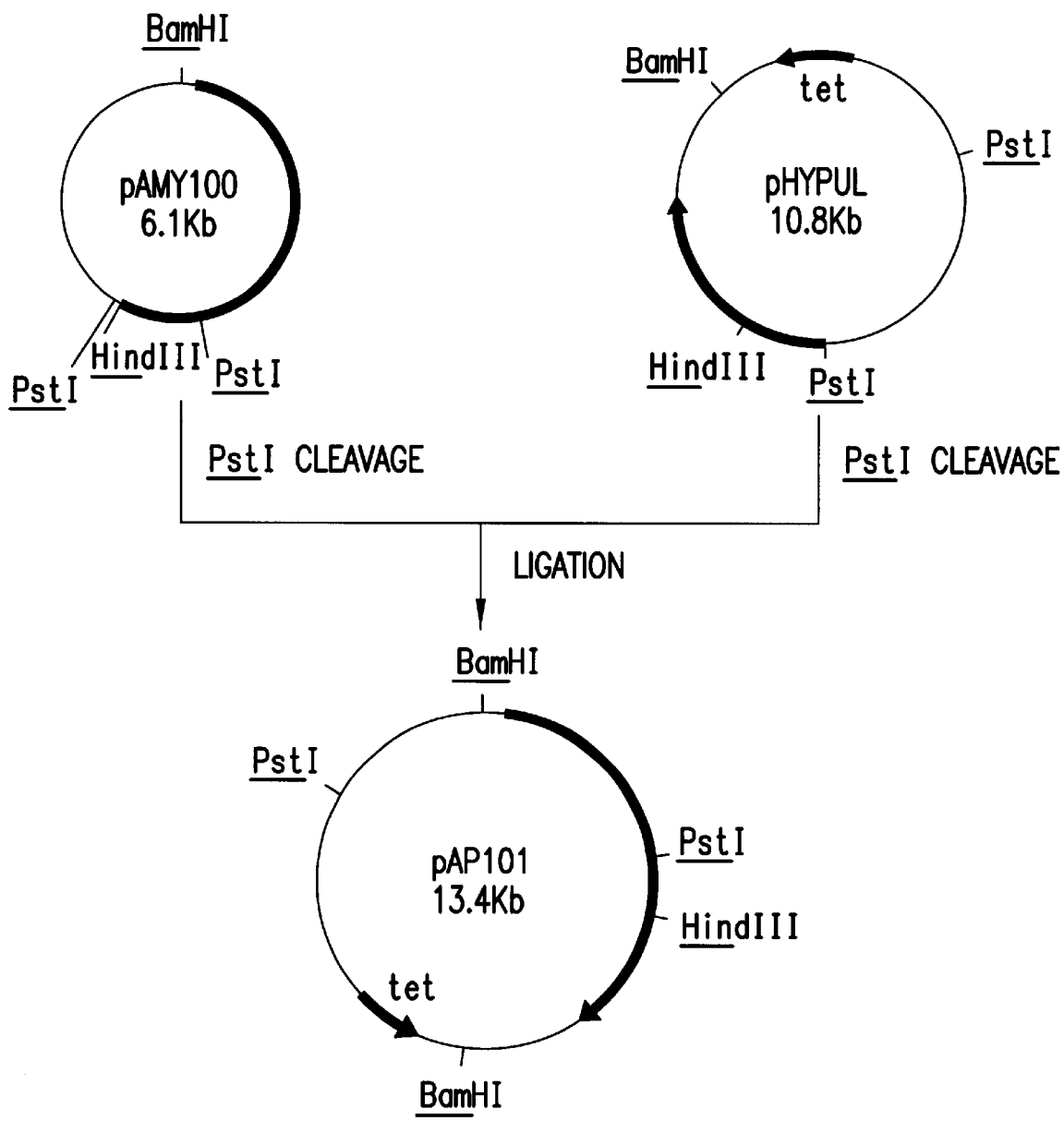
FIG. 2 is a scheme of subcloning of the alkaline amylopullulanase gene from Bacillus sp. KSM-AP1378.
Figure 3:
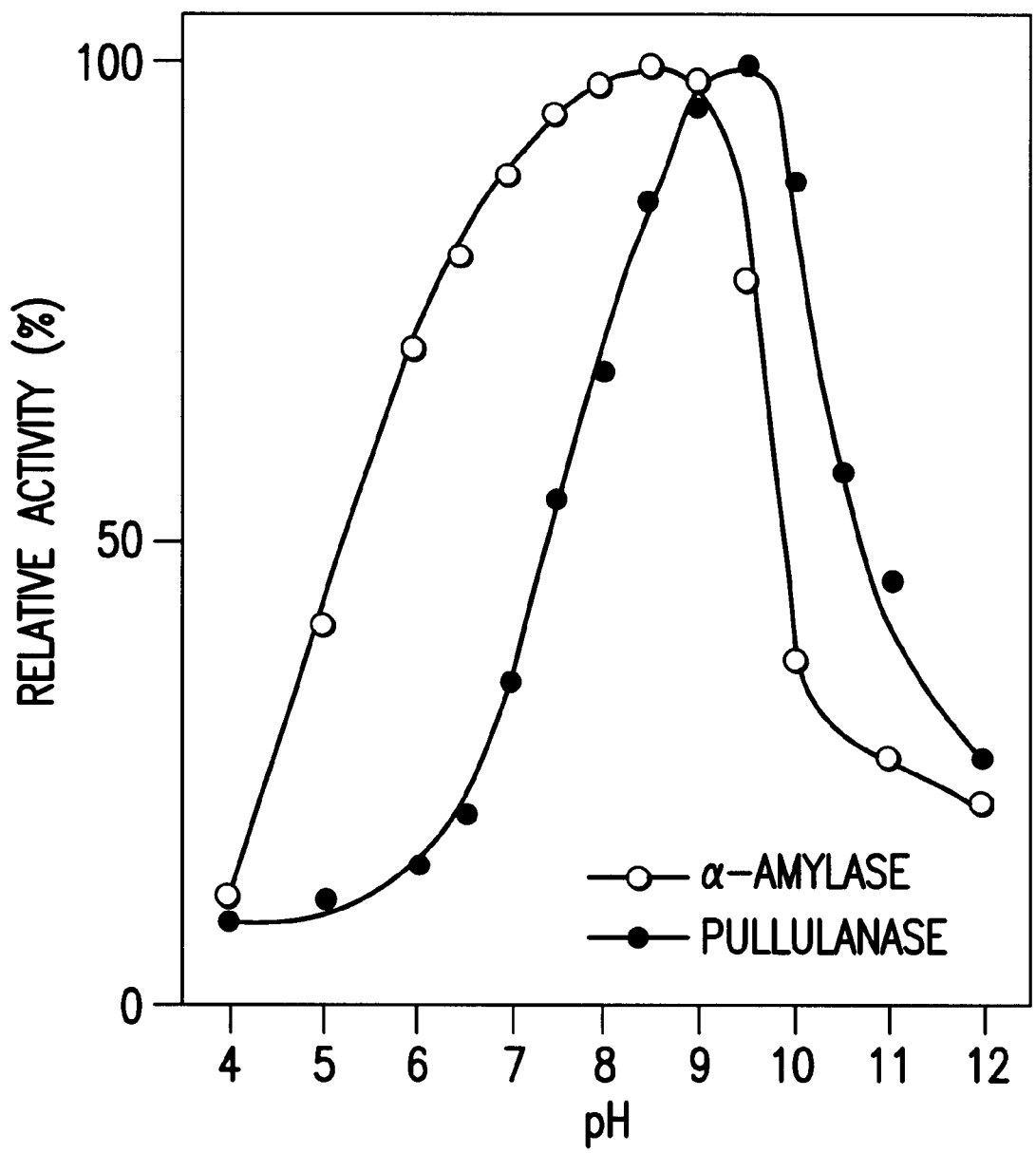
FIG. 3 is a graph showing the pH profiles of α-amylase activity and pullulanase activity of alkaline amylopullulanase.

An example of a preferred recombinant DNA containing the entire region of the alkaline amylopullulanase gene is plasmid pAP101 (FIG. 2). This plasmid has a size of 13.4 kb and is of a fragment containing the 6.2 kb alkaline amylopullulanase gene and part of pHY300PLK and pUC18. An example of a preferred recombinant microorganism harboring the recombinant DNA is an *E. coli* HB101(pAP101) strain. This strain is a product obtained by transforming *E. coli* HB101 strain with a recombinant plasmid, pAP101, using a standard transformation method. When this strain is cultured using a medium routinely employed for culturing *E. coli*, it produces alkaline amylopullulanase. The optimum reaction pHs of the thus-produced enzyme are pH 8–9 for the α-amylase activity and pH 9–10 for the pullulanase activity. This agrees well with the activity-pH relationship profiles determined for alkaline amylopullulanase produced by the gene donor bacterium Bacillus sp. KSM-AP1378 (FIG. 3).

The DNA fragments of the present invention are not necessarily limited only to those encoding the amino acid sequences shown in the below-described sequence listing so far as they encode a protein having the enzymatic activity of interest, and they encompass DNA fragments encoding an amino acid sequence in which one or more amino acids are substituted, added, deleted, inverted, or inserted. An example of such DNA is one encoding an amino acid sequence equivalent to the amino acid sequence described in SEQ ID NO:2 from which 32 amino acids on the N-terminal side have been deleted. Thus an alkaline amylopullulanase of SEQ ID NO:2 wherein between 1 to 32 amino acids have been deleted from the amino terminus is encompassed by the present invention.

When the thus-obtained transformants are cultured using known methods, alkaline α-amylase, alkaline pullulanase, or alkaline amylopullulanase can be produced. That is, if a transformant containing a domain encoding only alkaline α-amylase is used, alkaline α-amylase is obtained; if a transformant containing a domain encoding only alkaline pullulanase is used, alkaline pullulanase is obtained; and if a transformant containing a domain coding for the entire alkaline amylopullulanase is used, alkaline amylopullulanase is obtained.

The DNA fragments of the present invention may be further used as probes for the isolation of homologous alkaline amylopullulanase genes from other organisms.

EXAMPLES

The present invention will next be described in more detail by way of examples, which should not be construed as limiting the invention thereto. Concentrations in the Examples are all on a basis of % by weight.

Example 1

Isolation of Chromosomal DNA

Bacillus sp. KSM-AP1378 which produces alkaline amylopullulanase was inoculated into 5 ml of medium A (Table 1) and subjected to shaking culture at 30° C. for 24 hours. One ml of the culture was inoculated in 100 ml of the same medium, followed by shaking culture at 30° C. for a further 12 hours. Subsequently, cells were centrifugally collected and about 1 mg of chromosomal DNA was obtained in accordance with a method proposed by Saito and Miura (Saito, H. and Miura K., Biochim Biophys. Acta, 72, 619 (1963)).

TABLE 1

| Composition of medium A | |
|---|---|
| Pullulan | 1.0% |
| Tryptone | 0.2% |
| Yeast extract | 0.1% |
| $KH_2PO_4$ | 0.03% |
| $(NH_4)_2SO_4$ | 0.1% |
| $MgSO_4 \cdot 7H_2O$ | 0.02% |
| $CaCl_2 \cdot 2H_2O$ | 0.02% |
| $FeSO_4 \cdot 7H_2O$ | 0.001% |

TABLE 1-continued

| Composition of medium A | |
|---|---|
| $MnCl_2 \cdot 4H_2O$ | 0.0001% |
| $Na_2CO_3$ | 0.5% (separately sterilized) |
| | pH: 10 |

Example 2

Isolation of DNA Fragment Encoding Alkaline Pullulanase

The chromosomal DNA (10 μg) obtained in Example 1 was cleaved using a restriction enzyme PstI, after which a vector plasmid pBR322 (1 μg, Boehringer Mannheim) which had been cleaved likewise with PstI was added and a ligation reaction was caused using T4 DNA ligase, thereby producing a mixture of recombinant plasmids. A suspension of E. coli which had undergone transformation with the recombinant plasmid mixture was spread onto an LB agar plate medium (1.0% tryptone (Difco), 0.5% yeast extract (Difco), 1.0% NaCl, and 1.5% agar (Wako Pure Chemical)) containing 15 μg/ml of tetracycline and cultured at 37° C. for 12 hours. On the colonies of transformed cells which emerged, 0.8% agar containing 0.2% pullulan, 0.8% red pullulan (Kanno, M. and Tomiura, E., Agric. Biol. Chem., 49, 1529 (1985)), 1 mg/ml of lysozyme, and a glycine-NaCl—NaOH buffer (pH 9.0) was overlaid and reaction was caused at 37° C. for 5 hours. As a result, a single strain was obtained which formed a transparent halo around a colony of the strain due to decomposition of red pullulan. This strain was isolated as a recombinant microorganism capable of producing alkaline pullulanase.

Example 3

Restriction Map of Plasmid With Alkaline Pullulanase DNA

The recombinant microorganism obtained in Example 2 was inoculated into 5 ml of an LB medium (1.0% tryptone (Difco), 0.5% yeast extract (Difco), 1.0% NaCl1) containing 15 μg/ml of tetracycline and cultured at 37° C. overnight. Thereafter, the culture was transferred into 500 ml of an LB medium, followed by shaking culture for 24 hours. Cells were centrifugally collected from the culture, and about 500 mg of a recombinant plasmid was obtained using a standard method (Maniatis, T. et al., Molecular Cloning, Cold Spring Harbor Laboratory (1982)). From a restriction enzyme map of the resultant recombinant plasmid, it was found that the plasmid contained a PstI fragment (fragment A) of about 6.3 kb, as shown in FIG. 1. This plasmid was named pPU100. The E. coli HB101 strain transformed with the plasmid pPU100 was named HB100(pPU100).

Example 4

Measurement of Alkaline Pullulanase Activity

One ml of a culture of strain HB101(pPU100) which had been cultured overnight using 5 ml of an LB medium (containing tetracycline) was inoculated into 100 ml of an LB medium (containing tetracycline), followed by shaking culture at 37° C. for 24 hours. Subsequently, the cells collected through centrifugal separation were suspended in Tris-HCl buffer (pH 8.0) and the cells were disrupted by sonication. The cell debris was removed by centrifugal separation, and the supernatant was used as a cell-free extract. Similarly, a control cell-free extract was prepared using strain HB101(pBR322). Pullulanase activity of these extracts was measured. The pullulanase activity was measured by first causing a reaction in a reaction mixture containing 40 mM glycine-NaCl—NaOH buffer (pH 10) and pullulan (final concentration=0.25%) at 40° C. for 30 minutes, and the resultant reducing sugar was quantitatively determined by the 3,5-dinitrosalicylic acid (DNS) method (Miller, G. L., et al., Anal. Biochem., 2, 127 (1960)). The amount of enzyme which produces a quantity per minute of reducing sugar equivalent to 1 µmol of glucose is taken as 1 unit. As a result, pullulanase activity was detected in a cell-free extract of strain HB101(pPU100). Further, when the optimum working pH of the produced pullulanase was measured, it was found that the pullulanase was in fact an alkaline pullulanase having the optimum working pH of pH 9.5. For the measurement of enzymatic activity, the following buffers (each at 40 mM) were used:

pH 3.5–5.5: Acetate buffer
pH 5.5–8.5: Tris-maleic acid buffer
pH 8.5–10.5: Glycine-NaCl—NaOH buffer
pH 10.5–11.0: $Na_2CO_3$—$NaHCO_3$ buffer Example 5

Southern Hybridization of Alkaline Amylopullulanase Gene With PstI Digested Chromosomal DNAs of Bacillus sp. KSM-AP1378

Figure 4:
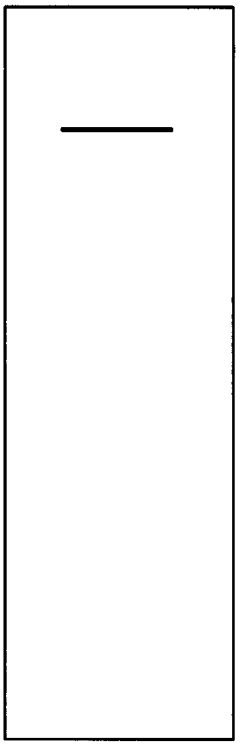
FIG. 4 shows the result of Southern hybridization analysis of PstI digestion products of the chromosomal DNA of a strain KSM-AP1378 from Bacillus sp. KSM-AP1378 using fragment A as a probe. On the left-hand side of the Southern filter, the positions of a size marker for lambda DNA-HindIII digestion products (Boehringer Mannheim) which simultaneously underwent electrophoresis are indicated together with the sizes of the respective DNA fragments.
Figure 5:
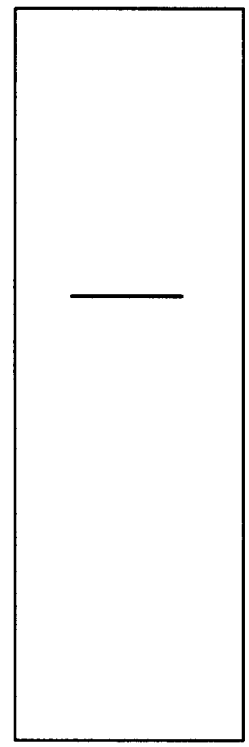
FIG. 5 shows the result of Southern hybridization analysis of XbaI digestion products of the chromosomal DNA of a strain KSM-AP1378 from Bacillus sp. KSM-AP1378 using fragment C as a probe. On the left-hand side of the Southern filter, the positions of a size marker for lambda DNA-HindIII digestion products (Boehringer Mannheim) which simultaneously underwent electrophoresis are indicated together with the sizes of the respective DNA fragments.

About 5 µg of pPU100 was cleaved with a restriction enzyme PstI and was then subjected to electrophoresis on an agarose gel. From the gel, about 0.5 µg of a PstI fragment having a size of about 6.3 kb was isolated using a Geneclean kit (Biolol Inc.). The PstI fragment was labelled using a DNA labelling & detection kit (Boehringer Mannheim) to prepare a probe DNA. Independently, chromosomal DNAs (3 µg each) derived from Bacillus sp. KSM-AP1378 cleaved with PstI were subjected to electrophoresis on an agarose gel, and the DNA bands were transferred onto a nylon membrane (Amersham) using a method proposed by Southern (Southern, E. M., *J. Mol. Biol.*, 98, 503 (1975)). Hybridization with the probe DNA was investigated using a DNA labelling & detection kit. As a result, in PstI cleavage products of chromosomal DNAs derived from the KSM-AP1378 strain, presence of a DNA fragment having a size of about 6.3 kb that hybridized with the probe DNA was detected as shown in FIG. 4. Thus, the PstI fragment having a size of about 6.3 kb contained in plasmid pPU100 was confirmed to be originated from the chromosomal DNA of Bacillus sp. KSM-AP1378.

Example 6

Construction of Plasmid Containing DNA Fragment Encoding Alkaline Pullulanase

A recombinant plasmid pHYPUL was created by inserting, between the PstI site and the BamHI site of plasmid pHY300PLK, a fragment having a size of about 3.5 kb (fragment B, FIG. 1) and obtained by cleaving a PstI fragment having a size of about 6.3 kb contained in plasmid pPU100 with BamHI. *E. coli* HB101 was transformed with the thus-created recombinant plasmid, and pullulanase activity was measured through a method similar to that of Example 4. As a result, a pullulanase activity having an optimum working pH in the pH range from 9 to 10 was observed. Thus, the essential domain of alkaline pullulanase was elucidated to be a stretch of about 3.5 kb from the PstI site to the BamHI site.

Example 7

Sequencing of DNA Fragments Encoding Alkaline Pullulanase

Using the fragment B obtained in Example 6, a commercially available deletion kit (Kilosequence Deletion kit, Takara Shuzo), and two suitable restriction enzymes, recombinant plasmid DNAs containing resultant reduced fragments were created, and the nucleotide sequences of the inserted fragments were determined. Nucleotide sequence was determined using a DNA sequencer (Model 370A, Applied Biosystems) and Taq-Dydeoxy Cycle Sequencing kit (Applied Biosystems) in accordance with a method using a fluorescent primer (Smith, L. M., et al., *Nature*, 321, 674 (1986)). By overlapping nucleotide sequences having sizes of about 300–450 bp from respective DNA samples, the 3038 bp sequence on the PstI site side of fragment B was determined. As a result, the open reading frame (ORF) of the alkaline pullulanase gene was found to continue to the upstream side of the PstI site, which is a terminus of the obtained fragment having a size of about 6.3 kb. Restriction Mapping of the Alkaline Amylopullulanase Gene Example 8

Using a fragment of about 6.3 kb as shown in FIG. 1, a PstI-XbaI 1.5 kb fragment (fragment C) was created, and labelled in a manner similar to that described in Example 5 to prepare a probe DNA (probe 1). Separately, chromosomal DNAs derived from Bacillus sp. KSM-AP1378 which had been cleaved with XbaI (3 µg each) were subjected to electrophoresis on an agarose gel, and the resultant DNA bands were transferred onto a nylon membrane (Amersham) in a manner similar to that described in Example 5, followed by hybridization with the probe. As a result, probe 1 was found to hybridize with an XbaI fragment having a size of about 2.3 kb, and from this, it was deduced that there exists an XbaI site about 0.8 kb upstream of a 6.3 kb fragment PstI-PstI on the chromosomal DNA derived from the KSM-AP1378 strain (FIG. 1). The stretch from the PstI site to the XbaI site having a length of about 0.8 kb was amplified using primers 1 and 2 (FIGS. 1 and 6) each having 24 nucleotides and synthesized based on the nucleotide sequence determined in Example 7, circular DNAs (which were obtained through intramolecular ligation of chromosomal DNA of KSM-AP1378 cleaved with XbaI) which served as templates, and a PCR kit (Applied Biosystems) in accordance with an inverse PCR method (Triglia, T. et al., *Nucleic Acids Res.*, 16, 81 (1988); one cycle=94° C.×1 min.+55° C.×1 min.+72° C.×3 min., 30 cycles). The sequence of the 0.8 kb fragment (fragment D) which had undergone the above amplification was determined in a manner similar to that described in Example 7. As a result, it was found that the ORF of alkaline pullulanase which continued from fragment C further extended to the upstream of fragment D (FIG. 1).

Example 9

Figure 7:
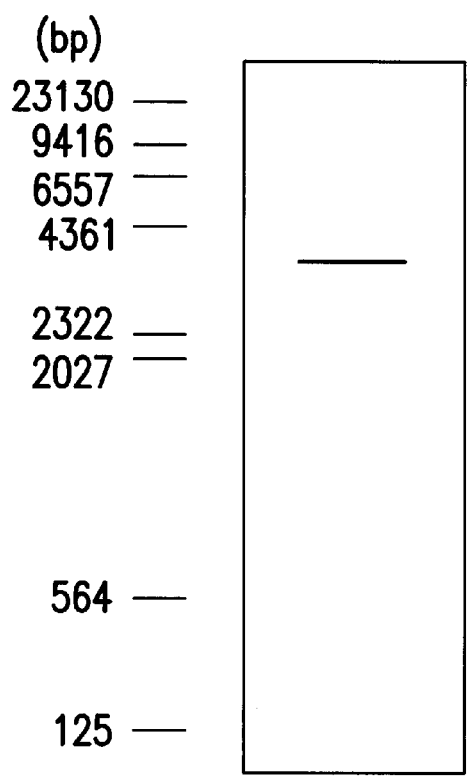
FIG. 7 shows the result of Southern hybridization analysis of EcoRI digestion products of the chromosomal DNA of a strain KSM-AP1378 from Bacillus sp. KSM-AP1378 using fragment D as a probe. On the left-hand side of the Southern filter, the positions of a size marker for lambda DNA-HindIII digestion products (Boehringer Mannheim) which simultaneously underwent electrophoresis are indicated together with the sizes of the respective DNA fragments.

The fragment having a size of about 0.8 kb and stretching from XbaI to PstI obtained in Example 8 was labelled in a manner similar to that described in Example 5 to prepare a probe DNA (probe 2). Separately, chromosomal DNAs derived from Bacillus sp. KSM-AP1378 which had been cleaved with EcoRI (3 μg each) were subjected to electrophoresis on an agarose gel, and the resultant DNA bands were transferred onto a nylon membrane (Amersham) in a manner similar to that described in Example 5, followed by hybridization with probe 2. From the size of a hybridized EcoRI fragment (3.6 kb, FIG. 7), it was deduced that there exists an EcoRI site 1.2 kb upstream of fragment D obtained in Example 8. The stretch from the XbaI site to 1.2 kb upstream of this site was amplified using primers 3 and 4 (FIGS. 1 and 6) having 24 nucleotides and synthesized based on the nucleotide sequence determined in Example 8 and circular DNAs (which were obtained through intramolecular ligation of chromosomal DNA of strain KSM-AP1378 cleaved with EcoRI) which served as templates in accordance with an inverse PCR method in a manner similar to that described in Example 8 (fragment E). The sequence of the 1.2 kb fragment which had undergone the above amplification was determined in a manner similar to that described in Example 7. As a result, it was found that the ORF of alkaline pullulanase which continued from fragment D further extended to the upstream of fragment E.

Example 10

Figure 8:
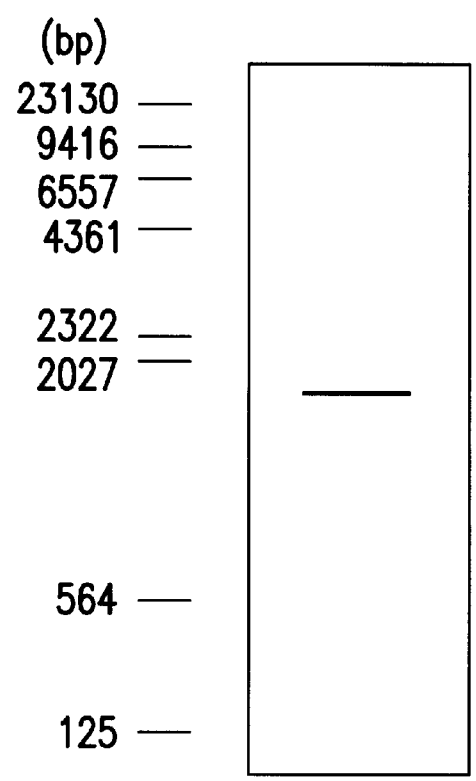
FIG. 8 shows the result of Southern hybridization analysis of XbaI digestion products of the chromosomal DNA of a strain KSM-AP1378 from Bacillus sp. KSM-AP1378 using fragment E as a probe. On the left-hand side of the Southern filter, the positions of a size marker for lambda DNA-HindIII digestion products (Boehringer Mannheim) which simultaneously underwent electrophoresis are indicated together with the sizes of the respective DNA fragments.

The fragment E obtained in Example 9 was labelled in a manner similar to that described in Example 5 to prepare a probe DNA (probe 3). In a manner similar to Examples 8 and 9, hybridization analysis was performed on XbaI cleavage products of the chromosomal DNA derived from strain KSM-AP1378 (FIG. 8). As a result, as shown in FIG. 1, it was deduced that there exists an XbaI site 1.1 kb upstream of the EcoRI site of fragment D in the chromosomal DNA derived from strain KSM-AP1378. The stretch from the EcoRI site to 1.1 kb upstream of this site was amplified using primers 5 and 6 (FIGS. 1 and 6 each having 24 nucleotides and synthesized based on the nucleotide sequence determined in Example 9 and circular DNAs (which were obtained through intramolecular ligation of chromosomal DNA of strain KSM-AP1378 cleaved with XbaI) which served as templates in accordance with an inverse PCR method in a manner similar to that described in Example 8. The sequence of the 1.1 kb fragment (fragment F) which had undergone the above amplification was determined in a manner similar to that described in Example 7. As a result, it was confirmed that the 5' region of the ORF of alkaline pullulanase gene which continued from fragment E existed in this fragment. The complete nucleotide sequence of the present gene and a deduced amino acid sequence are described in SEQ ID NO:1. Based on the fact that the putative sequence of Nos. 1 through 14 amino acids coincided with the sequence of amino terminus actually determined on Bacillus sp. KSM-AP1378 using alkaline amylopullulanase, it was presumed that the present gene encoded alkaline amylopullulanase.

Example 11

A 3.5 kb fragment (fragment G) containing an alkaline α-amylase domain of the alkaline amylopullulanase gene was amplified using primers A and B (FIGS. 1 and 6) each having 25 nucleotides and synthesized based on the nucleotide sequence determined in Examples 7 and 10, the chromosomal DNA of strain KSM-AP1378 as a template, and a PCR kit (Applied Biosystems) in accordance with a PCR method (one cycle=94° C.×1 min.+55° C.×1 min.+72° C.×3 min., 30 cycles). The resultant DNA fragment was inserted into the SmaI site of a pUC18 plasmid vector, and then subjected to transformation using commercially available E. coli HB101 competent cells. The obtained transformants were replicated onto an LB medium containing 0.4% blue starch (Starch azure, Sigma) and 50 μg/ml of ampicillin, followed by culturing at 37° C. for 12 hours. A single strain which decomposed blue starch and thus formed a halo around its colony was isolated. In a manner similar to that described in Example 3, a plasmid (pAMY100) was prepared from this strain.

Example 12

Recombinant Production of Alkaline Amylopullulanase

A recombinant plasmid mixture was prepared by ligating, using a T4 ligase, a 7.7 kb fragment obtained by cleaving a plasmid pHYPUL (Example 3) containing an alkaline pullulanase domain of the alkaline amylopullulanase and pAMY100 (Example 11) containing the alkaline α-amylase domain of the same gene. E. coli HB101 was transformed with the recombinant plasmid mixture, and each of transformants which emerged was replicated onto an LB medium containing 0.4% blue starch and 50 μg/ml of ampicillin and also onto another LB medium containing 0.8% red pullulan (Kanno, M. and Tomiura, E., Agric. Biol. Chem., 49, 1529 (1985)) and 50 μg/ml of ampicillin, followed by culturing for growth at 37° C. for 12 hours. A strain which formed a halo around its colony on both plates was isolated as a recombinant E. coli capable of producing the alkaline amylopullulanase.

Example 13

Using the recombinant E. coli obtained in Example 12, about 500 μg of a recombinant plasmid was prepared in a manner similar to that described in Example 3. From a restriction enzyme map of the resultant recombinant plasmid, it was found that the plasmid contained a DNA fragment (fragment H) of about 7.0 kb as shown in FIG. 1. This plasmid was named pAP101 (FIG. 2). E. coli HB101 transformed with the plasmid pAP101 was named HB101 (pAP101).

Example 14

A cell-free extract was prepared using E. coli HB101 (pAP101) in a manner similar to that described in Example 4. A control cell-free extract was also prepared using the HB101(pBR322) strain. α-Amylase and pullulanase activities of these extracts were measured. The α-amylase activity was measured by causing a reaction, at 50° C. for 15 minutes, in a reaction mixture containing 50 mM glycine-NaCl—NaOH buffer (pH 10) and soluble starch, and the resultant reducing sugar was quantitatively determined by the DNS method. The pullulanase activity was measured in a manner similar to that described in Example 4. In both cases, the amount of enzyme which produced a quantity per minute of reducing sugar equivalent to 1 μmol of glucose was taken as 1 unit. As a result, α-amylase and pullulanase activities were detected in a cell-free extract of strain HB101 (pAP101). When the optimum working pHs of α-amylase and pullulanase were measured as described in Example 4, it was found that the maximum α-amylase activity and the maximum pullulanase activity were observed in pH ranges from 8 to 9 and from 9 to 10, respectively.

Example 15

Characterization of Alkaline Amylopullulanase

To 50 mg of an alkaline amylopullulanase enzyme (210 kDa; Japanese Patent Publication (kokoku) No. 6-32613) purified from a culture of Bacillus sp. KSM-AP1378, 0.1 mg of papain (Sigma, 5 U/mg) was added and hydrolysis was allowed to proceed at 30° C. for 2 minutes. Subsequently, the reaction was stopped by the addition of 10 μg of antipain (Furuka). The resulting decomposition product was fractionated using a DEAE 5PW column (7.5 mm×7.5 cm; Tosoh) to obtain protein fragments with 114 kDa and 102 kDa. Measurement of enzymatic activities of these two protein fragments revealed that the 102 kDa protein fragment possessed only alkaline pullulanase activity and the 114 kDa protein fragment possessed only alkaline α-amylase activity. The N-terminus of the amino acid sequence of the 102 kDa protein fragment possessing only pullulanase activity was determined to have the sequence Thr-Val-Pro-Leu-Ala-Leu-Val-Ser-Gly-Glu-Val-Leu-Ser-Asp-Lys-Leu, which agreed perfectly with 1014th–1029th amino acids deduced from the amino acid sequence described in SEQ ID NO: 2. Similarly, the N-terminus of the amino acid sequence of the 114 kDa protein fragment possessing only α-amylase activity was determined to have the sequence Glu-Thr-Gly-Asp-Lys-Arg-Ile-Glu-Phe-Ser-Tyr-Glu-Arg-Pro, which agreed perfectly with 1st–14th amino acids deduced from the amino acid sequence described in SEQ ID NO: 2. These results also proved that the present gene encodes an alkaline amylopullulanase protein having different active centers, i.e., active centers for pullulanase activity and for α-amylase activity.

Example 16

The recombinant plasmid pAP101 was introduced in *B. subtilis* ISW1214 and the transformed cells were grown at 31° C. for 60 hours, with shaking, in LB medium containing 15 μg/ml of tetraglycine. The alkaline amylopullulanase was found to be excreted at a level of 60 units per liter, in terms of the alkaline pullulanase activity. The expressed enzymes had pH optima of around 8–9 for the amylase activity and at 9.5 for the pullulanase activity, values close to the pH optima for the respective enzymatic activities of the alkaline amylopullulanase of Bacillus sp. KSM-AP1378. The molecular mass of the expressed amylopullulanase protein was approximately 200–210 kDa by sodium dodecyl sulfate gel electrophoresis, a value close to the enzyme of strain KSM-AP1378.

Reference Example 1

A Bacillus sp. KSM-AP1378 strain which produces alkaline amylopullulanase was inoculated into 10 ml of medium A (Table 1) and subjected to shaking culture at 30° C. for 2 days. Ten (10) ml of the culture was inoculated in 1 liter of the same medium, followed by shaking culture at 30° C. for a further 3 days. Subsequently, cells were centrifugally processed to obtain a crude enzymatic liquid containing alkaline amylopullulanase. This crude enzymatic liquid was purified through various treatments including adsorption onto DEAE cellulose, affinity chromatography on a column of Sepharose-α-cyclodextrin, and gel filtration on a column of Sephacryl S-200 to obtain an electrophoretically homogeneous sample of the enzyme. Using a protein sequencer 476A (Applied Biosystems), the N-terminus of the amino acid sequence of this enzyme was determined to have the sequence Glu-Thr-Gly-Asp-Lys-Arg-Ile-Glu-Phe-Ser-Tyr-Glu-Arg-Pro.

Reference Example 2

The optimum pHs for the α-amylase activity and pullulanase activity of alkaline amylopullulanase obtained in Reference example 1 were determined using a method described in Examples 4 and 14. As a result, the optimum pH for α-amylase activity was observed in the vicinity of pH 8.5, and that for pullulanase activity was observed in the vicinity of pH 9.5.

INDUSTRIAL APPLICABILITY

According to the present invention, it is possible to obtain a gene coding for alkaline amylopullulanase exhibiting the maximum activity in an alkaline pH range as well as a microorganism harboring such gene. Use of the present invention facilitates mass production of alkaline amylopullulanase. Alkaline amylopullulanase is characteristic in that it has different active centers, one for α-amylase and one for pullulanase, in a single protein of the enzyme.

What is claimed is:

1. An isolated DNA fragment encoding an amylopullulanase which exhibits both alkaline pullulanase and alkaline α-amylase activities and having a nucleotide sequence shown in SEQ ID NO:1.

2. An isolated DNA fragment encoding alkaline α-amylase, wherein said alkaline α-amylase has an amino acid sequence of SEQ ID NO:3.

3. The isolated DNA fragment of claim 1, which further comprises a nucleotide sequence capable of regulating expression of a gene.

4. A recombinant DNA comprising the DNA fragment of claim 1.

5. A transformed microorganism comprising the recombinant DNA of claim 4.

6. A method for producing alkaline amylopullulanase, alkaline α-amylase, or alkaline pullulanase, comprising culturing the transformed microorganism of claim 5 and isolating the alkaline amylopullulanase, alkaline α-amylase or alkaline pullulanase produced by the microorganism.

7. An isolated DNA fragment encoding a protein exhibiting alkaline α-amylase activity and alkaline pullulanase activity, wherein said protein has an amino acid sequence shown in SEQ ID NO:2, wherein amino acids (−32) to (−1) are deleted.

8. An isolated DNA fragment encoding a protein exhibiting alkaline α-amylase activity, wherein said protein has an amino acid sequence shown in SEQ ID NO:3, wherein amino acids 1 to 32 are deleted.

* * * * *